United States Patent
Freedman et al.

(10) Patent No.: US 6,916,915 B1
(45) Date of Patent: Jul. 12, 2005

(54) STRESSOR REGULATED GENES

(75) Inventors: Jonathan H. Freedman, Rougemont, NC (US); Vivian H. C. Liao, Durham, NC (US)

(73) Assignee: Duke University, Durham, NC (US)

(*) Notice: Subject to any disclaimer, the term of this patent is extended or adjusted under 35 U.S.C. 154(b) by 0 days.

(21) Appl. No.: 09/437,450

(22) Filed: Nov. 10, 1999

Related U.S. Application Data

(60) Provisional application No. 60/109,281, filed on Nov. 20, 1998.

(51) Int. Cl.$^7$ .......................... C07H 21/00; C07H 21/02

(52) U.S. Cl. ...................... 536/23.1; 536/24.3

(58) Field of Search ............... 536/23.1, 24.3, 536/23.5; 800/13; 435/320.1, 325

(56) References Cited

PUBLICATIONS

Gardener, A., GenBank Acc. No. Z81529, "*Caenorhabditis elegans* cosmid F35E8, complete sequence," US Natl. Library of Med., Berthesda, MD, Sep. 21, 1998, accessed by PTO on Jul. 6, 2004.*

N. Ishii et al., Medicine, Accession No. 93040228.*

J. Freedman et al., Journal of Biological Chemistry, "Novel Metallothionein Genes of *Caenorhabditis elegans*," Feb. 1993, vol. 268, No. 4, pp. 2554–2564.*

Liao and Freedman, "Cadmium–regulated Genes from the Nematode *Caenorhabditis elegans*", The Journal of Biological Chemistry 273(48):31962–31970 (1998).

* cited by examiner

*Primary Examiner*—Scott D. Priebe
(74) *Attorney, Agent, or Firm*—Nixon & Vanderhye P.C.

(57) ABSTRACT

The present invention relates, in general, to stressor-responsive genes and, in particular, to metal-responsive genes, to mRNAs, to proteins encoded therein and to uses thereof, for example, as biomonitors and in drug discovery.

8 Claims, 43 Drawing Sheets

Fig. 5A-1

```
LOCUS       AF072438     284 bp     mRNA        EST     06-JUL-1998
DEFINITION  AF072438 mRNA from cadmium-responsive gene Caenorhabditis elegans
            cDNA clone DDRT21, mRNA sequence.
ACCESSION   AF072438
NID         g3288944
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1 (bases 1 to 284)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
            Email: jonf@duke.edu.
FEATURES             Location/Qualifiers
     source          1..284
                     /organism="Caenorhabditis elegans"
                     /strain="N2"
                     /db_xref="taxon:6239"
                     /clone="DDRT21"
                     /clone_lib="mRNA from cadmium-responsive gene"
                     /tissue_type="whole animal"
                     /dev_stage="mixed population"
BASE COUNT      88 a    61 c    54 g    81 t
ORIGIN
        1 tggtactcca cacggacaaa tacatttagt tttacaagcc gccacgcgac acgcaacggc
       61 cgtaaatcta cccaaggtac aacaacaaca tgtcaagcac agacccatat cttatttgtg
      121 cggaaggatg gcctctactg tagtaatcga caattggact cttatccacc ggatcactta
      181 acctattttg atattaatat gcctgattgg ggatcacagg gtttgcccga aaatgtaatt
      241 atgaactgaa ttcgaaatgt atttataaat tagtttttat tggg
//

LOCUS       AF072437     214 bp     mRNA        EST     06-JUL-1998
DEFINITION  AF072437 mRNA from cadmium-responsive gene Caenorhabditis elegans
            cDNA clone VL8, mRNA sequence.
ACCESSION   AF072437
NID         g3288943
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1 (bases 1 to 214)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
```

Fig. 5A-2

```
                differential display
  JOURNAL   Unpublished (1998)
COMMENT
          Contact: Jonathan H. Freedman
          Nicholas School of the Environment
          Duke University
          Box 90328, Durham, NC 27708-0328, USA
          Email: jonf@duke.edu.
FEATURES           Location/Qualifiers
    source      1..214
              /organism="Caenorhabditis elegans"
              /strain="N2"
              /db_xref="taxon:6239"
              /clone="VL8"
              /clone_lib="mRNA from cadmium-responsive gene"
              /tissue_type="whole animal"
              /dev_stage="mixed population"
BASE COUNT       68 a     37 c    66 g    43 t
ORIGIN
      1 gcaagtgcgg agacaaatgt gaatgcagtg gagacaagtg ttgtgagaag tactgctgtg
     61 aggaggccag tgagaaaaaa tgctgtccag ctggatgtaa gggagactgc aagtgtgcaa
    121 actgtcattg tgcagagcag aagcagtgcg agacaagacc catcaacacc agggaactgc
    181 tgcggctcat taaaatgttt cagagttgaa tcta
//

LOCUS       AF072436     217 bp    mRNA      EST    06-JUL-1998
DEFINITION  AF072436 mRNA from cadmium-responsive gene Caenorhabditis elegans
            cDNA clone VL7, mRNA sequence.
ACCESSION   AF072436
NID         g3288942
KEYWORDS    EST.
SOURCE      Caenorhabditis elegans.
 ORGANISM   Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1 (bases 1 to 217)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
          Contact: Jonathan H. Freedman
          Nicholas School of the Environment
          Duke University
          Box 90328, Durham, NC 27708-0328, USA
          Email: jonf@duke.edu.
FEATURES           Location/Qualifiers
    source      1..217
              /organism="Caenorhabditis elegans"
              /strain="N2"
              /db_xref="taxon:6239"
              /clone="VL7"
              /clone_lib="mRNA from cadmium-responsive gene"
```

Fig. 5A-3

```
            /tissue_type="whole animal"
            /dev_stage="mixed population"
BASE COUNT      69 a    37 c    66 g    45 t
ORIGIN
     1 ttagcaagtg cggagacaaa tgtgaatgca gtggagacaa gtgttgtgag aagtactgct
    61 gtgaggaggc cagtgagaaa aaatgctgtc cagctggatg taagggagac tgcaagtgtg
   121 caaactgtca ttgtgcagag cagaagcagt gcgagacaag acccatcaac accagggaac
   181 tgctgcggct cattaaaatg tttcagagtt gaatcta
//

LOCUS       AF072435     217 bp    mRNA          EST    06-JUL-1998
DEFINITION  AF072435 mRNA from cadmium-responsive gene Caenorhabditis elegans
            cDNA clone VL15, mRNA sequence.
ACCESSION   AF072435
NID         g3288941
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 217)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
            Email: jonf@duke.edu.
FEATURES             Location/Qualifiers
     source          1..217
                     /organism="Caenorhabditis elegans"
                     /strain="N2"
                     /db_xref="taxon:6239"
                     /clone="VL15"
                     /clone_lib="mRNA from cadmium-responsive gene"
                     /tissue_type="whole animal"
                     /dev_stage="mixed population"
BASE COUNT      69 a    37 c    66 g    45 t
ORIGIN
     1 ttagcaagtg cggagacaaa tgtgaatgca gtggagacaa gtgttgtgag aagtactgct
    61 gtgaggaggc cagtgagaaa aaatgctgtc cagctggatg taagggagac tgcaagtgtg
   121 caaactgtca ttgtgcagag cagaagcagt gcgagacaag acccatcaac accagggaac
   181 tgctgcggct cattaaaatg tttcagagtt gaatcta
//

LOCUS       AF072434     216 bp    mRNA          EST    06-JUL-1998
DEFINITION  AF072434 mRNA from cadmium-responsive gene Caenorhabditis elegans
            cDNA clone VL12, mRNA sequence.
ACCESSION   AF072434
NID         g3288940
```

Fig. 5A-4

```
KEYWORDS  EST.
SOURCE    Caenorhabditis elegans.
 ORGANISM Caenorhabditis elegans
          Eukaryota; Metazoa; Nematoda; Secernentea; Rhabditia; Rhabditida;
          Rhabditina; Rhabditoidea; Rhabditidae; Peloderinae; Caenorhabditis.
REFERENCE  1  (bases 1 to 216)
  AUTHORS  Freedman,J.H. and Liao,H.-C.
  TITLE    Cadmium-Regulated Genes from the Nematode Caenorhabditis elegans.
           Identification and cloning of new cadmium-responsive genes by
           differential display
  JOURNAL  Unpublished (1998)
COMMENT
           Contact: Jonathan H. Freedman
           Nicholas School of the Environment
           Duke University
           Box 90328, Durham, NC 27708-0328, USA
           Email: jonf@duke.edu.
FEATURES           Location/Qualifiers
     source        1..216
                   /organism="Caenorhabditis elegans"
                   /strain="N2"
                   /db_xref="taxon:6239"
                   /clone="VL12"
                   /clone_lib="mRNA from cadmium-responsive gene"
                   /tissue_type="whole animal"
                   /dev_stage="mixed population"
BASE COUNT      69 a    37 c    66 g    44 t
ORIGIN
        1 tagcaagtgc ggagacaaat gtgaatgcag tggagacaag tgttgtgaga agtactgctg
       61 tgaggaggcc agtgagaaaa aatgctgtcc agctggatgt aagggagact gcaagtgtgc
      121 aaactgtcat tgtgcagagc agaagcagtg cgagacaaga cccatcaaca ccagggaact
      181 gctgcggctc attaaaatgt ttcagagttg aatcta
//

LOCUS       AF071399        240 bp    mRNA            EST       01-JUL-1998
DEFINITION  AF071399 mRNA from cadmium-responsive gene Caenorhabditis elegans
            cDNA clone DDRT9A, mRNA sequence.
ACCESSION   AF071399
NID         g3265144
KEYWORDS    EST.
SOURCE      Caenorhabditis elegans.
 ORGANISM   Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 240)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
```

Box 90328, Durham, NC 27708-0328, USA
Email: jonf@duke.edu.

Fig. 5A-5

FEATURES          Location/Qualifiers
     source       1..240
                  /organism="Caenorhabditis elegans"
                  /strain="N2"
                  /db_xref="taxon:6239"
                  /clone="DDRT9A"
                  /clone_lib="mRNA from cadmium-responsive gene"
                  /tissue_type="whole animal"
                  /dev_stage="mixed population"
BASE COUNT    81 a   28 c   41 g   90 t
ORIGIN
     1 tttttttt ttgagactat gaatatttaa tttagcaagc gaatttgttg ttattagata
    61 ggaagcctag aagagtgaaa attttaaaaa atgtgaggaa ctggttttgt attcagaagc
   121 atataaacgt tgtcttaatt tatatatgac gttctctatg aatataagcca aaatgatcga
   181 tattttaat ccaaaaatca aacatttttg gtatacgaac ctcgccttca cggaggttta
//

LOCUS       AF071398      217 bp    mRNA            EST      01-JUL-1998
DEFINITION  AF071398 mRNA from cadmium-responsive gene Caenorhabditis elegans
            cDNA clone DDRT7, mRNA sequence.
ACCESSION   AF071398
NID         g3265143
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 217)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
            Email: jonf@duke.edu.
FEATURES          Location/Qualifiers
     source       1..217
                  /organism="Caenorhabditis elegans"
                  /strain="N2"
                  /db_xref="taxon:6239"
                  /clone="DDRT7"
                  /clone_lib="mRNA from cadmium-responsive gene"
                  /tissue_type="whole animal"
                  /dev_stage="mixed population"
BASE COUNT    64 a   38 c   42 g   73 t
ORIGIN
     1 tttttttt ttttgggagg aaatcacggc ggcggatcga acagtcttct ctcaattggc
    61 aactgtctat atcattccgc aatcacattt cggatgttct cgaaaaggca ttccaaagtt

Fig. 5A-6

```
    121 attggagtca tgtgaaagag ttcgtcatga agtttaccca aaggcatttc atagtgaatt
    181 aaattgtcaa actagtagtc agatcaataa aattttc
//

LOCUS       AF071397     219 bp    mRNA         EST         01-JUL-1998
DEFINITION  AF071397 mRNA from cadmium-responsive gene Caenorhabditis elegans
            cDNA clone DDRT6, mRNA sequence.
ACCESSION   AF071397
NID         g3265142
KEYWORDS    EST.
SOURCE      Caenorhabditis elegans.
 ORGANISM   Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 219)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
            Email: jonf@duke.edu.
FEATURES             Location/Qualifiers
     source          1..219
                     /organism="Caenorhabditis elegans"
                     /strain="N2"
                     /db_xref="taxon:6239"
                     /clone="DDRT6"
                     /clone_lib="mRNA from cadmium-responsive gene"
                     /tissue_type="whole animal"
                     /dev_stage="mixed population"
BASE COUNT       75 a     38 c     34 g     72 t
ORIGIN
      1 tttttttt tttgacgaca aattatttag aaatattgca taagcgaaaa tacaatttga
     61 cccgtagcaa aaaaatacat gtcgggaaaa tgagaaaaat ggttaataaa tttttaaaaa
    121 aagtatataa ttcctccaac aagctactgc atgtccttgt actacaatct tctccgacgg
    181 attccactct cgatcgcgga ttcggattct tcatgttgg
//

LOCUS       AF071396     254 bp    mRNA         EST         01-JUL-1998
DEFINITION  AF071396 mRNA from cadmium-responsive gene Caenorhabditis elegans
            cDNA clone DDRT5, mRNA sequence.
ACCESSION   AF071396
NID         g3265141
KEYWORDS    EST.
SOURCE      Caenorhabditis elegans.
 ORGANISM   Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 254)
```

Fig. 5A-7

```
AUTHORS   Freedman,J.H. and Liao,H.-C.
TITLE     Cadmium-Regulated Genes from the Nematode Caenorhabditis elegans.
          Identification and cloning of new cadmium-responsive genes by
          differential display
JOURNAL   Unpublished (1998)
COMMENT
          Contact: Jonathan H. Freedman
          Nicholas School of the Environment
          Duke University
          Box 90328, Durham, NC 27708-0328, USA
          Email: jonf@duke.edu.
FEATURES          Location/Qualifiers
     source    1..254
                 /organism="Caenorhabditis elegans"
                 /strain="N2"
                 /db_xref="taxon:6239"
                 /clone="DDRT5"
                 /clone_lib="mRNA from cadmium-responsive gene"
                 /tissue_type="whole animal"
                 /dev_stage="mixed population"
BASE COUNT      79 a    43 c    50 g    82 t
ORIGIN
        1 tttttttt ttttgccca tcggaaaata gcaagcctct ccacaggtac agtaattgag
       61 catttggatg atgcttcttc acagcattat ccagtgtata cttatccttt ttcgtaagag
      121 tttcgaaaaa atgtccataa aaagtgttga atgacttttg ttcatctcga agcatacata
      181 cgatcgaaac ggagaaatcg atagatcgaa tcaggataag tggggatact gtattgtcgg
      241 atgaaaacat agac
//

LOCUS       AF071394        165 bp    mRNA            EST       01-JUL-1998
DEFINITION  AF071394 mRNA from cadmium-responsive gene Caenorhabditis elegans
            cDNA clone DDRT47, mRNA sequence.
ACCESSION   AF071394
NID         g3265139
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 165)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
          Contact: Jonathan H. Freedman
          Nicholas School of the Environment
          Duke University
          Box 90328, Durham, NC 27708-0328, USA
          Email: jonf@duke.edu.
FEATURES          Location/Qualifiers
     source    1..165
                 /organism="Caenorhabditis elegans"
```

Fig. 5A-8

```
             /strain="N2"
             /db_xref="taxon:6239"
             /clone="DDRT47"
             /clone_lib="mRNA from cadmium-responsive gene"
             /tissue_type="whole animal"
             /dev_stage="mixed population"
BASE COUNT       38 a     37 c     20 g     70 t
ORIGIN
        1 ttttttttt tttccaacc ccttcacata ataggcggaa aaccgattgt tgctgttact
       61 tgttgttgtg tttattcect gacctatcca tattcccttc ttcccaatct ctaaagatat
      121 acctgaaaac gagtttttg aatacttgat acatttgtct tcatc
//

LOCUS       AF071393     154 bp    mRNA         EST        01-JUL-1998
DEFINITION  AF071393 mRNA from cadmium-responsive gene Caenorhabditis elegans
            cDNA clone DDRT41, mRNA sequence.
ACCESSION   AF071393
NID         g3265138
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1 (bases 1 to 154)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
            Email: jonf@duke.edu.
FEATURES             Location/Qualifiers
     source          1..154
                     /organism="Caenorhabditis elegans"
                     /strain="N2"
                     /db_xref="taxon:6239"
                     /clone="DDRT41"
                     /clone_lib="mRNA from cadmium-responsive gene"
                     /tissue_type="whole animal"
                     /dev_stage="mixed population"
BASE COUNT       49 a     27 c     40 g     38 t
ORIGIN
        1 tggattgtgc gggtggtact gccaagtctg gtcgtgatag aaaacatcag gcgatcatgc
       61 ctttacgtgg taagatcctg aacgtcgaaa agcaatggaa cataagatct acgaaaatga
      121 ggagatcaaa aacatgttta cagctttggt ccta
//

LOCUS       AF071392     264 bp    mRNA         EST        01-JUL-1998
DEFINITION  AF071392 mRNA from cadmium-responsive gene Caenorhabditis elegans
            cDNA clone DDRT40, mRNA sequence.
```

Fig. 5A-9

```
ACCESSION   AF071392
NID         g3265137
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 264)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
            Email: jonf@duke.edu.
FEATURES            Location/Qualifiers
     source         1..264
                    /organism="Caenorhabditis elegans"
                    /strain="N2"
                    /db_xref="taxon:6239"
                    /clone="DDRT40"
                    /clone_lib="mRNA from cadmium-responsive gene"
                    /tissue_type="whole animal"
                    /dev_stage="mixed population"
BASE COUNT      90 a     47 c     59 g     68 t
ORIGIN
        1 tggattgtgc ggagtataag caaaaatttc tggaaaagtc gggtgatatg aagtttgata
       61 agatcttcaa tcaaaagctc ggtttcttgt tgttaaaaga ttccgcagga aaatgtctcc
      121 gagagtccgt gtcctcaaat taaattctac gaggcgatca aagaatacga gaaaatggag
      181 acaccagatg agcgattaac aaaagcacga gaaatttatc gatcatcata tacggttgaa
      241 ttccgtcgcg caatcgtcac actc
//

LOCUS       AF071391     187 bp    mRNA            EST       01-JUL-1998
DEFINITION  AF071391 mRNA from cadmium-responsive gene Caenorhabditis elegans
            cDNA clone DDRT4, mRNA sequence.
ACCESSION   AF071391
NID         g3265136
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 187)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
```

Fig. 5A-10

```
       Contact: Jonathan H. Freedman
       Nicholas School of the Environment
       Duke University
       Box 90328, Durham, NC 27708-0328, USA
       Email: jonf@duke.edu.
FEATURES           Location/Qualifiers
     source       1..187
                  /organism="Caenorhabditis elegans"
                  /strain="N2"
                  /db_xref="taxon:6239"
                  /clone="DDRT4"
                  /clone_lib="mRNA from cadmium-responsive gene"
                  /tissue_type="whole animal"
                  /dev_stage="mixed population"
BASE COUNT       57 a    22 c    41 g    67 t
ORIGIN
     1 aaattttat taaaataaaa taaacatgtt tttgttgata ttatagcgtt aaagctgaaa
    61 tgacaatgat tagaaaacca gcagagaata gagatgatgt tcctttcgtt gttgtttcca
   121 gtgaacactt gttgcggtgg agcccgtatt tagcgagtgg tagtttttga tgtgattggt
   181 tccaatc
//

LOCUS     AF071389   267 bp   mRNA        EST    01-JUL-1998
DEFINITION AF071389 mRNA from cadmium-responsive gene Caenorhabditis elegans
           cDNA clone DDRT37, mRNA sequence.
ACCESSION AF071389
NID      g3265134
KEYWORDS  EST.
SOURCE    Caenorhabditis elegans.
 ORGANISM Caenorhabditis elegans
          Eukaryota; Metazoa; Nematoda; Secernentea; Rhabditia; Rhabditida;
          Rhabditina; Rhabditoidea; Rhabditidae; Peloderinae; Caenorhabditis.
REFERENCE 1 (bases 1 to 267)
  AUTHORS Freedman,J.H. and Liao,H.-C.
  TITLE   Cadmium-Regulated Genes from the Nematode Caenorhabditis elegans.
          Identification and cloning of new cadmium-responsive genes by
          differential display
  JOURNAL Unpublished (1998)
COMMENT
       Contact: Jonathan H. Freedman
       Nicholas School of the Environment
       Duke University
       Box 90328, Durham, NC 27708-0328, USA
       Email: jonf@duke.edu.
FEATURES           Location/Qualifiers
     source       1..267
                  /organism="Caenorhabditis elegans"
                  /strain="N2"
                  /db_xref="taxon:6239"
                  /clone="DDRT37"
                  /clone_lib="mRNA from cadmium-responsive gene"
                  /tissue_type="whole animal"
                  /dev_stage="mixed population"
BASE COUNT       66 a    75 c    54 g    72 t
```

*Fig. 5A-11*

ORIGIN
```
  1 tggtactcca cctacaagtt ctacaagttc tacgaggttg tcctgatcga tccattccac
 61 aaggctatcc gtcgtaaccc agacacccaa tggatcacca agcctagttc acaagcaccg
121 tgagcaaaga ggactcacct ctgctggacg caagttcgtg gactcggaaa gggattgctt
181 ttctctgcta cccgcggagg atcccaacac caaagtttt ccacccgcca accgataaat
241 cttgttattt tattttgttt tgggttt
//
```

LOCUS     AF071388     292 bp     mRNA       EST     01-JUL-1998
DEFINITION  AF071388 mRNA from cadmium-responsive gene Caenorhabditis elegans
       cDNA clone DDRT36, mRNA sequence.
ACCESSION   AF071388
NID        g3265133
KEYWORDS   EST.
SOURCE     Caenorhabditis elegans.
  ORGANISM  Caenorhabditis elegans
       Eukaryota; Metazoa; Nematoda; Secernentea; Rhabditia; Rhabditida;
       Rhabditina; Rhabditoidea; Rhabditidae; Peloderinae; Caenorhabditis.
REFERENCE   1  (bases 1 to 292)
  AUTHORS   Freedman,J.H. and Liao,H.-C.
  TITLE     Cadmium-Regulated Genes from the Nematode Caenorhabditis elegans.
       Identification and cloning of new cadmium-responsive genes by
       differential display
  JOURNAL   Unpublished (1998)
COMMENT
       Contact: Jonathan H. Freedman
       Nicholas School of the Environment
       Duke University
       Box 90328, Durham, NC 27708-0328, USA
       Email: jonf@duke.edu.
FEATURES         Location/Qualifiers
    source      1..292
            /organism="Caenorhabditis elegans"
            /strain="N2"
            /db_xref="taxon:6239"
            /clone="DDRT36"
            /clone_lib="mRNA from cadmium-responsive gene"
            /tissue_type="whole animal"
            /dev_stage="mixed population"
BASE COUNT     73 a    57 c    51 g    111 t
ORIGIN
```
  1 tttttttt tttcccaac cccttcacat aaaggcggaa aaccgattgt tgctgttact
 61 tgttgttgtc gtttattccc tgaggtatcc atattccgct tctcccaatc tctaaagata
121 tacctgaaaa cgagttgtcg tcgaaatact tgatacatgt tgtcttcatc ctggtgtatg
181 ttgtttcgca aattcttcat actagttatg ataggatttg aatgagctgg cacgagtcaa
241 ctttgaactc gaatttcaat attttcgtga tcctgcatta agtgatgaat aa
//
```

LOCUS     AF071387     314 bp     mRNA       EST     01-JUL-1998
DEFINITION  AF071387 mRNA from cadmium-responsive gene Caenorhabditis elegans
       cDNA clone DDRT35, mRNA sequence.
ACCESSION   AF071387
NID        g3265132
KEYWORDS   EST.

Fig. 5A-12

```
SOURCE    Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE  1  (bases 1 to 314)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
            Email: jonf@duke.edu.
FEATURES           Location/Qualifiers
     source        1..314
                   /organism="Caenorhabditis elegans"
                   /strain="N2"
                   /db_xref="taxon:6239"
                   /clone="DDRT35"
                   /clone_lib="mRNA from cadmium-responsive gene"
                   /tissue_type="whole animal"
                   /dev_stage="mixed population"
BASE COUNT     86 a    65 c    56 g    107 t
ORIGIN
        1 tctgagctag gaggtccagg aggaaacaac ggaggaggtg ctggaaatgg tggattcgac
       61 gattttgatg atttggctcg ccgtttcgaa gaactgaaaa agattaagta atcatcaccc
      121 gacgttccat tccttattaa ctatttgttt ctcttccacc caattttttt ttcacgtgtc
      181 ttttttttgta tcataaatga gacccccaaa aactagctgt ttcttagtgc atacgttaaa
      241 accccttttag tcattgatta tcattgtata cctcattatc cgaaaaacct ttcgacattc
      301 atcaactagg tttt
//

LOCUS       AF071386     189 bp    mRNA         EST       01-JUL-1998
DEFINITION  AF071386 mRNA from cadmium-responsive gene Caenorhabditis elegans
            cDNA clone DDRT34, mRNA sequence.
ACCESSION   AF071386
NID         g3265131
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 189)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
```

Fig. 5A-13

Duke University
Box 90328, Durham, NC 27708-0328, USA
Email: jonf@duke.edu.
FEATURES        Location/Qualifiers
    source        1..189
                /organism="Caenorhabditis elegans"
                /strain="N2"
                /db_xref="taxon:6239"
                /clone="DDRT34"
                /clone_lib="mRNA from cadmium-responsive gene"
                /tissue_type="whole animal"
                /dev_stage="mixed population"
BASE COUNT     61 a   26 c   48 g   54 t
ORIGIN
    1 tctgagctag ggaccgaaat tcacaaatat ccaattgtta ctggatggtg gggatgtgga
   61 cgatttaatg gggacaagcc actgaagtgt atgttatttc attcgttaaa tatgaagatg
  121 gaggagagtg aatggggatt ttgcttcttt tgcaaaatgg cctccctatg tacctgaaaa
  181 aaaaaaaaa
//

LOCUS       AF071385     171 bp    mRNA        EST    01-JUL-1998
DEFINITION  AF071385 mRNA from cadmium-responsive gene Caenorhabditis elegans
            cDNA clone DDRT33D, mRNA sequence.
ACCESSION   AF071385
NID         g3265130
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1 (bases 1 to 171)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
            Email: jonf@duke.edu.
FEATURES        Location/Qualifiers
    source        1..171
                /organism="Caenorhabditis elegans"
                /strain="N2"
                /db_xref="taxon:6239"
                /clone="DDRT33D"
                /clone_lib="mRNA from cadmium-responsive gene"
                /tissue_type="whole animal"
                /dev_stage="mixed population"
BASE COUNT     57 a   44 c   37 g   33 t
ORIGIN
    1 tctgagctag gaaaggacgg agaagatgga gagaacggag ctgctggagc cgctggacca

Fig. 5A-14

```
 61 aagggatctt gcgaccactg cccaccacca cgcactcccc aggatattaa ttcacttctc
121 tctaatttta gtgaatctca ttctaataaa aagccgcccc aaaaaaaaaa a
//

LOCUS       AF071383     289 bp    mRNA         EST      01-JUL-1998
DEFINITION  AF071383 mRNA from cadmium-responsive gene Caenorhabditis elegans
            cDNA clone DDRT30, mRNA sequence.
ACCESSION   AF071383
NID         g3265128
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 289)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
            Email: jonf@duke.edu.
FEATURES             Location/Qualifiers
     source          1..289
                     /organism="Caenorhabditis elegans"
                     /strain="N2"
                     /db_xref="taxon:6239"
                     /clone="DDRT30"
                     /clone_lib="mRNA from cadmium-responsive gene"
                     /tissue_type="whole animal"
                     /dev_stage="mixed population"
BASE COUNT       68 a     64 c     63 g     94 t
ORIGIN
   1 tttttttt tttgagcgag cgtttattat ttgagtcgag cttgggttga gtcgtcagct
  61 gaacatgaag attgacaaag aagacgatca gcagcaacag atgcgcagag tcgcattctt
 121 tgcggttgct gtctcaactg cagccgtcat ttcaagcatc gtgactctcc caatgatcta
 181 ctcttactct tcaatctttc caatcccatt tgatcattgg aaaccgagtt ctgtaaaact
 241 gtgctcgtga tatgtggtgt cgaagttctc cacaagtcag gtgtaccct
//

LOCUS       AF071382     162 bp    mRNA         EST      01-JUL-1998
DEFINITION  AF071382 mRNA from cadmium-responsive gene Caenorhabditis elegans
            cDNA clone DDRT3, mRNA sequence.
ACCESSION   AF071382
NID         g3265127
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
```

Fig. 5A-15

```
REFERENCE   1  (bases 1 to 162)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
            Email: jonf@duke.edu.
FEATURES             Location/Qualifiers
     source          1..162
                     /organism="Caenorhabditis elegans"
                     /strain="N2"
                     /db_xref="taxon:6239"
                     /clone="DDRT3"
                     /clone_lib="mRNA from cadmium-responsive gene"
                     /tissue_type="whole animal"
                     /dev_stage="mixed population"
BASE COUNT       64 a    31 c    18 g    49 t
ORIGIN
        1 ctccaccgca acaagtgttc acgtggaaac aacaacgaaa ggaacatcat ctctatctct
       61 gctggttttc taatcattgt catttcagct ttaacgctat aatcaacaaa aacagtttat
      121 tttattttaa taaaaattta ttcgtgcaaa aaaaaaaaaa aa
//

LOCUS       AF071381      140 bp    mRNA           EST       01-JUL-1998
DEFINITION  AF071381 mRNA from cadmium-responsive gene Caenorhabditis elegans
            cDNA clone DDRT29, mRNA sequence.
ACCESSION   AF071381
NID         g3265126
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 140)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
            Email: jonf@duke.edu.
FEATURES             Location/Qualifiers
     source          1..140
                     /organism="Caenorhabditis elegans"
                     /strain="N2"
```

Fig. 5A-16

```
            /db_xref="taxon:6239"
            /clone="DDRT29"
            /clone_lib="mRNA from cadmium-responsive gene"
            /tissue_type="whole animal"
            /dev_stage="mixed population"
BASE COUNT     52 a    25 c    29 g    34 t
ORIGIN
     1 tagggcctgg ttgtgacaat gtgcactaaa atggggcatg aatatcacca gcagagttca
    61 cttacccaaa gtgtacttat taagagtcaa ctgtgaagta tatgagacat ttcagttgcc
   121 tgcccaaaaa aaaaaaaaaa
//

LOCUS       AF071380      308 bp    mRNA            EST      01-JUL-1998
DEFINITION  AF071380 mRNA from cadmium-responsive gene Caenorhabditis elegans
            cDNA clone DDRT28, mRNA sequence.
ACCESSION   AF071380
NID         g3265125
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1 (bases 1 to 308)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
            Email: jonf@duke.edu.
FEATURES             Location/Qualifiers
     source          1..308
                     /organism="Caenorhabditis elegans"
                     /strain="N2"
                     /db_xref="taxon:6239"
                     /clone="DDRT28"
                     /clone_lib="mRNA from cadmium-responsive gene"
                     /tissue_type="whole animal"
                     /dev_stage="mixed population"
BASE COUNT     88 a    70 c    73 g    77 t
ORIGIN
     1 tagttaggca caggatgtac gaggaaattc tactattttc gggtctcacc acgaaatcac
    61 aataacccgg atttttagt ggtccccgca cgttgaccta ctggcgcgtc aggcactccg
   121 ccgcgacatt cgccgacacg cctacaatcc acgtgtcaat cgtcagattt gcggatcaat
   181 aatggtgatg aaaggtggaa atacgtatat ggatcatgtt caaaggcatc aagctgaaca
   241 attcgaagag ttgaatcggc gtcgacactt ttgatccaag accgtaagaa atttgaaagc
   301 tattggtg
//

LOCUS       AF071379      238 bp    mRNA            EST      01-JUL-1998
```

Fig. 5A-17

DEFINITION AF071379 mRNA from cadmium-responsive gene Caenorhabditis elegans
cDNA clone DDRT26, mRNA sequence.
ACCESSION AF071379
NID     g3265124
KEYWORDS EST.
SOURCE  Caenorhabditis elegans.
 ORGANISM Caenorhabditis elegans
        Eukaryota; Metazoa; Nematoda; Secernentea; Rhabditia; Rhabditida;
        Rhabditina; Rhabditoidea; Rhabditidae; Peloderinae; Caenorhabditis.
REFERENCE 1 (bases 1 to 238)
 AUTHORS Freedman,J.H. and Liao,H.-C.
 TITLE   Cadmium-Regulated Genes from the Nematode Caenorhabditis elegans.
         Identification and cloning of new cadmium-responsive genes by
         differential display
 JOURNAL Unpublished (1998)
COMMENT
        Contact: Jonathan H. Freedman
        Nicholas School of the Environment
        Duke University
        Box 90328, Durham, NC 27708-0328, USA
        Email: jonf@duke.edu.
FEATURES        Location/Qualifiers
    source     1..238
               /organism="Caenorhabditis elegans"
               /strain="N2"
               /db_xref="taxon:6239"
               /clone="DDRT26"
               /clone_lib="mRNA from cadmium-responsive gene"
               /tissue_type="whole animal"
               /dev_stage="mixed population"
BASE COUNT     74 a    43 c    44 g    77 t
ORIGIN
    1 tttttttt ttttggggag gaaatcacgg cttcggatgc aacagtcttc tctcaattgg
   61 caactgtcta ttatccattc cgcaatcaca tttcggatgt tctcgaaaag gacttcccaa
  121 agttattgga gtactgtgaa agagttcgtc atgaagttta cccaaaggac tttactatgt
  181 gaattaaatt gtcaaactag tagtcagatc aataaaattt tccgcgcgaa aaaaaaaa
//

LOCUS    AF071378    324 bp    mRNA       EST    01-JUL-1998
DEFINITION AF071378 mRNA from cadmium-responsive gene Caenorhabditis elegans
cDNA clone DDRT25A, mRNA sequence.
ACCESSION AF071378
NID     g3265123
KEYWORDS EST.
SOURCE  Caenorhabditis elegans.
 ORGANISM Caenorhabditis elegans
        Eukaryota; Metazoa; Nematoda; Secernentea; Rhabditia; Rhabditida;
        Rhabditina; Rhabditoidea; Rhabditidae; Peloderinae; Caenorhabditis.
REFERENCE 1 (bases 1 to 324)
 AUTHORS Freedman,J.H. and Liao,H.-C.
 TITLE   Cadmium-Regulated Genes from the Nematode Caenorhabditis elegans.
         Identification and cloning of new cadmium-responsive genes by
         differential display
 JOURNAL Unpublished (1998)

Fig. 5A-18

```
COMMENT
        Contact: Jonathan H. Freedman
        Nicholas School of the Environment
        Duke University
        Box 90328, Durham, NC 27708-0328, USA
        Email: jonf@duke.edu.
FEATURES         Location/Qualifiers
    source       1..324
                 /organism="Caenorhabditis elegans"
                 /strain="N2"
                 /db_xref="taxon:6239"
                 /clone="DDRT25A"
                 /clone_lib="mRNA from cadmium-responsive gene"
                 /tissue_type="whole animal"
                 /dev_stage="mixed population"
BASE COUNT     102 a    70 c    73 g    79 t
ORIGIN
      1 tagttaggca caggatgtac gaggaaattc tactattttc gggtctcacc acgaaatcac
     61 aataacccgg atttttagt ggtccccgca cgttgaccta cttggcgcgt caggcactcc
    121 gccgcgacat tcgccgacac gcctacaatc cacgtgtcaa tcgtcagatt tgcggatcaa
    181 taatggtgat gaaaggtgga aatacgtata tggatcatgt tcaaaggcat caagctgaac
    241 aattcgaaga gttgaatcgg cgtcgacaac tttttgatcc aagaccgtaa gaaatttgaa
    301 agctattggt gaaaaaaaaa aaaa
//

LOCUS       AF071377     272 bp    mRNA         EST      01-JUL-1998
DEFINITION  AF071377 mRNA from cadmium-responsive gene Caenorhabditis elegans
            cDNA clone DDRT24, mRNA sequence.
ACCESSION   AF071377
NID         g3265122
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 272)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
        Contact: Jonathan H. Freedman
        Nicholas School of the Environment
        Duke University
        Box 90328, Durham, NC 27708-0328, USA
        Email: jonf@duke.edu.
FEATURES         Location/Qualifiers
    source       1..272
                 /organism="Caenorhabditis elegans"
                 /strain="N2"
                 /db_xref="taxon:6239"
                 /clone="DDRT24"
                 /clone_lib="mRNA from cadmium-responsive gene"
```

Fig. 5A-19

```
            /tissue_type="whole animal"
            /dev_stage="mixed population"
BASE COUNT      91 a     74 c     51 g    56 t
ORIGIN
    1 tggtactcca cgcagaaaga agaaggtcat ccacaacacc gctactaccg atgacaagaa
   61 gcttcaaagc aatttgaaga aactctctgt caccaacatt ccaggaatcg aggaggtcaa
  121 catgattaag acgatggaac cgttatccac ttcaacaacc caaaagtcta aacctctgtt
  181 cccagccaat accttctctg tcacaggatc agccgataac aagtcagatc actgaaatgt
  241 ctcccaggga atgctgaact ggtcagagtc ct
//

LOCUS       AF071395     218 bp    rRNA          INV    30-JUN-1998
DEFINITION  Caenorhabditis elegans strain N2 clone DDRT48, rRNA sequence.
ACCESSION   AF071395
NID         g3265140
KEYWORDS
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 218)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished
REFERENCE   2  (bases 1 to 218)
  AUTHORS   Freedman,J.H. and Liao,H.-C.
  TITLE     Direct Submission
  JOURNAL   Submitted (09-JUN-1998) Nicholas School of the Environment, Duke
            University, Box 90328, Durham, NC 27708-0328, USA
FEATURES             Location/Qualifiers
     source          1..218
                     /organism="Caenorhabditis elegans"
                     /strain="N2"
                     /db_xref="taxon:6239"
                     /tissue_type="whole animal"
                     /dev_stage="mixed population"
                     /note="from cadmium-responsive gene"
                     /clone="DDRT48"
     misc_RNA        1..218
                     /note="similar to Caenorhabditis elegans rDNA tandem
                     repeats"
BASE COUNT      58 a     58 c     38 g    64 t
ORIGIN
    1 tttttttt ttcgacaag cggggactaa aagcaagctt ttcatccacc gatgatacaa
   61 ggcgttttta gtaccttagg atcgactgac ccacatccaa ctactgttcc acgtggaacc
  121 cttctccact tcagtcttca aggatcgaac ttgaatattt gctactacca tacgatctgc
  181 actgacggaa agtccagccg agcctacctc atagttaa
//

LOCUS       AF071390     238 bp    rRNA          INV    30-JUN-1998
DEFINITION  Caenorhabditis elegans strain N2 clone DDRT38, rRNA sequence.
ACCESSION   AF071390
```

Fig. 5A-20

```
NID      g3265135
KEYWORDS
SOURCE   Caenorhabditis elegans.
 ORGANISM  Caenorhabditis elegans
         Eukaryota; Metazoa; Nematoda; Secernentea; Rhabditia; Rhabditida;
         Rhabditina; Rhabditoidea; Rhabditidae; Peloderinae; Caenorhabditis.
REFERENCE  1  (bases 1 to 238)
 AUTHORS   Freedman,J.H. and Liao,H.-C.
 TITLE     Cadmium-Regulated Genes from the Nematode Caenorhabditis elegans.
           Identification and cloning of new cadmium-responsive genes by
           differential display
 JOURNAL   Unpublished
REFERENCE  2  (bases 1 to 238)
 AUTHORS   Freedman,J.H. and Liao,H.-C.
 TITLE     Direct Submission
 JOURNAL   Submitted (09-JUN-1998) Nicholas School of the Environment, Duke
           University, Box 90328, Durham, NC 27708-0328, USA
FEATURES         Location/Qualifiers
     source     1..238
                /organism="Caenorhabditis elegans"
                /strain="N2"
                /db_xref="taxon:6239"
                /tissue_type="whole animal"
                /dev_stage="mixed population"
                /note="from cadmium-responsive gene"
                /clone="DDRT38"
     misc_RNA   1..238
                /note="similar to Caenorhabditis elegans rDNA tandem
                repeats"
BASE COUNT     58 a    50 c    58 g    72 t
ORIGIN
     1 ttttttttt ttttgccggg cggtgtgtac aaccggcagg gacgtaatca acgtgagctg
    61 atgactcgcg cttactaggc attcctcgtt taagggcaat aattacaata ccctatcccg
   121 gacatggaag aatttcaacg gtttaccgat acctttcaac acgggaaaac tacccggttg
   181 gacaccatta ggactgacag attgaaagtc tttgtcgatt tggtggttgg ttgtgcat
//

LOCUS      AF071384       253 bp    rRNA            INV       30-JUN-1998
DEFINITION  Caenorhabditis elegans strain N2 clone DDRT32, rRNA sequence.
ACCESSION   AF071384
NID         g3265129
KEYWORDS
SOURCE   Caenorhabditis elegans.
 ORGANISM  Caenorhabditis elegans
         Eukaryota; Metazoa; Nematoda; Secernentea; Rhabditia; Rhabditida;
         Rhabditina; Rhabditoidea; Rhabditidae; Peloderinae; Caenorhabditis.
REFERENCE  1  (bases 1 to 253)
 AUTHORS   Freedman,J.H. and Liao,H.-C.
 TITLE     Cadmium-Regulated Genes from the Nematode Caenorhabditis elegans.
           Identification and cloning of new cadmium-responsive genes by
           differential display
 JOURNAL   Unpublished
REFERENCE  2  (bases 1 to 253)
 AUTHORS   Freedman,J.H. and Liao,H.-C.
```

Fig. 5A-21

```
     TITLE    Direct Submission
     JOURNAL  Submitted (09-JUN-1998) Nicholas School of the Environment, Duke
              University, Box 90328, Durham, NC 27708-0328, USA
     FEATURES         Location/Qualifiers
          source     1..253
                     /organism="Caenorhabditis elegans"
                     /strain="N2"
                     /db_xref="taxon:6239"
                     /tissue_type="whole animal"
                     /dev_stage="mixed population"
                     /note="from cadmium-responsive gene"
                     /clone="DDRT32"
          misc_RNA   1..253
                     /note="similar to Caenorhabditis elegans rDNA tandem
                     repeats"
     BASE COUNT       45 a    60 c    69 g    79 t
     ORIGIN
           1 tagggcctgt tggttgatgc ttgtccggcg cagttctgtc tgcttgatac ttcgggttga
          61 tggcggacta gtgattgtgc ttcttgcgga ccgtttctgg tgtgtgcttg gacctcggtt
         121 ctagtatcct gatcgctcat ctatcaaccg tactgtaacc ggtacgactc agggaatccg
         181 actgtctaat taaaacagag gtgacagatg gtccttgcgg acgttaactg tcactgattt
         241 ctccccagtg cac
     //

LOCUS       AF071376       277 bp    rRNA             INV      30-JUN-1998
     DEFINITION  Caenorhabditis elegans strain N2 clone DDRT23, rRNA sequence.
     ACCESSION   AF071376
     NID         g3265121
     KEYWORDS
     SOURCE      Caenorhabditis elegans.
       ORGANISM  Caenorhabditis elegans
                 Eukaryota; Metazoa; Nematoda; Secernentea; Rhabditia; Rhabditida;
                 Rhabditina; Rhabditoidea; Rhabditidae; Peloderinae; Caenorhabditis.
     REFERENCE   1  (bases 1 to 277)
       AUTHORS   Freedman,J.H. and Liao,H.-C.
       TITLE     Cadmium-Regulated Genes from the Nematode Caenorhabditis elegans.
                 Identification and cloning of new cadmium-responsive genes by
                 differential display
       JOURNAL   Unpublished
     REFERENCE   2  (bases 1 to 277)
       AUTHORS   Freedman,J.H. and Liao,H.-C.
       TITLE     Direct Submission
       JOURNAL   Submitted (09-JUN-1998) Nicholas School of the Environment, Duke
                 University, Box 90328, Durham, NC 27708-0328, USA
     FEATURES         Location/Qualifiers
          source     1..277
                     /organism="Caenorhabditis elegans"
                     /strain="N2"
                     /db_xref="taxon:6239"
                     /tissue_type="whole animal"
                     /dev_stage="mixed population"
                     /note="from cadmium-responsive gene"
                     /clone="DDRT23"
          misc_RNA   1..277
```

Fig. 5A-22

```
            /note="similar to Caenorhabditis elegans rDNA tandem
                repeats"
BASE COUNT     67 a    59 c    73 g    78 t
ORIGIN
       1 tttttttttt tttgggggggg gcggtgtgta caaagggcag ggacgtaatc aacgtgagct
      61 gatgactcac acttctaggc attcctcgtt taagggaata attacaatac ccatcccgga
     121 catggaagaa tttcaacggt ttaccgatac cctttcggca acacgggaaa actcacccgg
     181 tccggacacc attaggactg acagattgaa agctctttct cgatttggtg gttggtggtg
     241 catggccgtt cttagttggt ggagtaccaa tcactag
//

LOCUS       AF071375    216 bp    mRNA         EST      30-JUN-1998
DEFINITION  AF071375 mRNA from cadmium-responsive gene Caenorhabditis elegans
            cDNA clone VL5, mRNA sequence.
ACCESSION   AF071375
NID         g3265120
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 216)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
            Email: jonf@duke.edu.
FEATURES             Location/Qualifiers
     source          1..216
                     /organism="Caenorhabditis elegans"
                     /strain="N2"
                     /db_xref="taxon:6239"
                     /clone="VL5"
                     /clone_lib="mRNA from cadmium-responsive gene"
                     /tissue_type="whole animal"
                     /dev_stage="mixed population"
BASE COUNT     69 a    37 c    66 g    44 t
ORIGIN
       1 tagcaagtgc ggagacaaat gtgaatgcag tggagacaag tgttgtgaga agtactgctg
      61 tgaggaggcc agtgagaaaa aatgctgtcc agctggatgt aagggagact gcaagtgtgc
     121 aaactgtcat tgtgcagagc agaagcagtg cgagacaaga cccatcaaca ccagggaact
     181 gctgcggctc attaaaatgt ttcagagttg aatcta
//

LOCUS       AF071374    356 bp    mRNA         EST      30-JUN-1998
DEFINITION  AF071374 mRNA from cadmium-responsive gene Caenorhabditis elegans
            cDNA clone VL9, mRNA sequence.
ACCESSION   AF071374
```

Fig. 5A-23

```
NID      g3265119
KEYWORDS EST.
SOURCE   Caenorhabditis elegans.
 ORGANISM Caenorhabditis elegans
          Eukaryota; Metazoa; Nematoda; Secernentea; Rhabditia; Rhabditida;
          Rhabditina; Rhabditoidea; Rhabditidae; Peloderinae; Caenorhabditis.
REFERENCE 1 (bases 1 to 356)
  AUTHORS  Freedman,J.H. and Liao,H.-C.
  TITLE    Cadmium-Regulated Genes from the Nematode Caenorhabditis elegans.
           Identification and cloning of new cadmium-responsive genes by
           differential display
  JOURNAL  Unpublished (1998)
COMMENT
           Contact: Jonathan H. Freedman
           Nicholas School of the Environment
           Duke University
           Box 90328, Durham, NC 27708-0328, USA
           Email: jonf@duke.edu.
FEATURES          Location/Qualifiers
     source       1..356
                  /organism="Caenorhabditis elegans"
                  /strain="N2"
                  /db_xref="taxon:6239"
                  /clone="VL9"
                  /clone_lib="mRNA from cadmium-responsive gene"
                  /tissue_type="whole animal"
                  /dev_stage="mixed population"
BASE COUNT    126 a   70 c   55 g   105 t
ORIGIN
        1 caatcgatga gtatcctcgt acaattaatg catgatgcaa ttggaaatat tccgaggtag
       61 gtaaaacggg gaacatcacg agatagatga atacagcgga tatcatatag gcacgcagaa
      121 tatcaataaa attttcaaat tttcaaaata tcataacgat tataacacgt agcagggaat
      181 tttaaagcca ctgaaataaa tatagaataa tatatacaga cacacacaat ctagatttca
      241 gaacattttc agtaacgacg tttgaactt tttgaagatt tcgccgagcc tttgatcact
      301 tttgcagtca caacttccac aactttcttt tcctcctctt cctctacatc gattgc
//

LOCUS       AF071373    199 bp    mRNA        EST    30-JUN-1998
DEFINITION  AF071373 mRNA from cadmium-responsive gene Caenorhabditis elegans
            cDNA clone VL3A, mRNA sequence.
ACCESSION   AF071373
NID      g3265118
KEYWORDS EST.
SOURCE   Caenorhabditis elegans.
 ORGANISM Caenorhabditis elegans
          Eukaryota; Metazoa; Nematoda; Secernentea; Rhabditia; Rhabditida;
          Rhabditina; Rhabditoidea; Rhabditidae; Peloderinae; Caenorhabditis.
REFERENCE 1 (bases 1 to 199)
  AUTHORS  Freedman,J.H. and Liao,H.-C.
  TITLE    Cadmium-Regulated Genes from the Nematode Caenorhabditis elegans.
           Identification and cloning of new cadmium-responsive genes by
           differential display
  JOURNAL  Unpublished (1998)
COMMENT
```

Fig. 5A-24

```
            Contact: Jonathan H. Freedman
            Nicholas School of the Environment
            Duke University
            Box 90328, Durham, NC 27708-0328, USA
            Email: jonf@duke.edu.
FEATURES            Location/Qualifiers
     source     1..199
                     /organism="Caenorhabditis elegans"
                     /strain="N2"
                     /db_xref="taxon:6239"
                     /clone="VL3A"
                     /clone_lib="mRNA from cadmium-responsive gene"
                     /tissue_type="whole animal"
                     /dev_stage="mixed population"
BASE COUNT    55 a   31 c   20 g   93 t
ORIGIN
    1 taaactctat gtttatttgt tttttcaaat ttcaaattga aaattgaaac tttcaatttg
   61 attagagtct ttgtggtttg actccttttt ttcattgaac atcttttacg tacgtcatac
  121 ttttgtatac acatttacaa atgttgtttt gtaattatat gtaacaaatt tctatgtaca
  181 cctcatctca tctctctat
//

LOCUS       AF071372       326 bp    mRNA        EST       30-JUN-1998
DEFINITION  AF071372 mRNA from cadmium-responsive gene Caenorhabditis elegans
            cDNA clone VL21A, mRNA sequence.
ACCESSION   AF071372
NID         g3265117
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 326)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
            Email: jonf@duke.edu.
FEATURES            Location/Qualifiers
     source     1..326
                     /organism="Caenorhabditis elegans"
                     /strain="N2"
                     /db_xref="taxon:6239"
                     /clone="VL21A"
                     /clone_lib="mRNA from cadmium-responsive gene"
                     /tissue_type="whole animal"
                     /dev_stage="mixed population"
BASE COUNT    76 a   61 c   59 g   130 t
```

Fig. 5A-25

ORIGIN
       1 cgtctccctt ttttacttac ttgtaggtgc gtcttgtcaa ttgtacgtac ttatatttag
      61 caaacctctg gtgttacctc tgcttttttg taaaatttgt tacacacttt cttttggca
     121 gtaaaagttg tttagcacac tttaacactc tgccactacc aaggtaatag tgagcccatc
     181 gaggttttat aaatgtcctt gatagtttaa agtgttggag gatcgagcta ctttggtagt
     241 ggaaagccgt gtttcttgtc ttgttttgtt cgatgatttta cccaactatt tgatattttg
     301 atttaccgga ttatataata cacccc
//

LOCUS       AF071371    147 bp    mRNA        EST    30-JUN-1998
DEFINITION  AF071371 mRNA from cadmium-responsive gene Caenorhabditis elegans
            cDNA clone VL20B, mRNA sequence.
ACCESSION   AF071371
NID         g3265116
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1 (bases 1 to 147)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
            Email: jonf@duke.edu.
FEATURES             Location/Qualifiers
     source          1..147
                     /organism="Caenorhabditis elegans"
                     /strain="N2"
                     /db_xref="taxon:6239"
                     /clone="VL20B"
                     /clone_lib="mRNA from cadmium-responsive gene"
                     /tissue_type="whole animal"
                     /dev_stage="mixed population"
BASE COUNT     54 a   27 c   22 g   44 t
ORIGIN
       1 tggcaatata cctagaaaga gtaaatatta tgacgtggca ataatacaga agcagtccga
      61 actacaactc acgaaacatt ttgaaagttt acctcttgat ttcttttgaa tgttttgtct
     121 cacacaataa agaaaattct accgtac
//

LOCUS       AF071370    285 bp    mRNA        EST    30-JUN-1998
DEFINITION  AF071370 mRNA from cadmium-responsive gene Caenorhabditis elegans
            cDNA clone VL19, mRNA sequence.
ACCESSION   AF071370
NID         g3265115
KEYWORDS    EST.
SOURCE      Caenorhabditis elegans.

Fig. 5A-26

```
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 285)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
            Email: jonf@duke.edu.
FEATURES             Location/Qualifiers
     source          1..285
                     /organism="Caenorhabditis elegans"
                     /strain="N2"
                     /db_xref="taxon:6239"
                     /clone="VL19"
                     /clone_lib="mRNA from cadmium-responsive gene"
                     /tissue_type="whole animal"
                     /dev_stage="mixed population"
BASE COUNT      91 a     46 c     52 g     96 t
ORIGIN
        1 cgtggcaata cacagaatat acacattgag atggttcgaa tggcaaagag aaggtggtgg
       61 ctaatcattc tatatagcac aacgccaaat ataatttcga tgtggcggaa tttgtgatgg
      121 tgaatggaat taacaaaatt ttctaaacgt cttcattccg agtaattttt cgtttttccct
      181 ccactttcg atttatattg ttttcttaga aaaagtattt attgcatcgg gtgctcattg
      241 tctttgtgta gaatataaac tcgttcactt cccaaaaaaa aaaaa
//

LOCUS       AF071369      216 bp    mRNA            EST       30-JUN-1998
DEFINITION  AF071369 mRNA from cadmium-responsive gene Caenorhabditis elegans
            cDNA clone VL13, mRNA sequence.
ACCESSION   AF071369
NID         g3265114
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 216)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
```

Email: jonf@duke.edu.

Fig. 5A-27

```
FEATURES          Location/Qualifiers
     source        1..216
                   /organism="Caenorhabditis elegans"
                   /strain="N2"
                   /db_xref="taxon:6239"
                   /clone="VL13"
                   /clone_lib="mRNA from cadmium-responsive gene"
                   /tissue_type="whole animal"
                   /dev_stage="mixed population"
BASE COUNT       69 a    37 c    66 g    44 t
ORIGIN
      1 tagcaagtcg gagacaaatg tgaatgcagt ggagacaagt gttgtgagaa gtactgctgt
     61 gaggaggcca gtgagaaaaa atgctgtcca gctggatgta agggagactg caagtgtgca
    121 aactgtcatt gtgcagagca gaagcagtgc ggagacaaga cccatcaaca ccagggaact
    181 gctgcggctc attaaaatgt ttcagagttg aatcta
//

LOCUS       AF071368    142 bp   mRNA        EST     30-JUN-1998
DEFINITION  AF071368 mRNA from cadmium-responsive gene Caenorhabditis elegans
            cDNA clone VL11, mRNA sequence.
ACCESSION   AF071368
NID         g3265113
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 142)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
            Email: jonf@duke.edu.
FEATURES          Location/Qualifiers
     source        1..142
                   /organism="Caenorhabditis elegans"
                   /strain="N2"
                   /db_xref="taxon:6239"
                   /clone="VL11"
                   /clone_lib="mRNA from cadmium-responsive gene"
                   /tissue_type="whole animal"
                   /dev_stage="mixed population"
BASE COUNT       45 a    21 c    23 g    53 t
ORIGIN
      1 gtgctggagt tgtttgtatt tcagaataaa taaaataaaa tatgatttga gtagaatatt
     61 aaaataaagt ccttcacatt aaattatcaa ttgcttggcc tcgaatatct tccagctggt
    121 gattgcattc gttcattcct tc
```

LOCUS       AF071367      84 bp    mRNA         EST    30-JUN-1998
DEFINITION  AF071367 mRNA from cadmium-responsive gene Caenorhabditis elegans
            cDNA clone VL10, mRNA sequence.
ACCESSION   AF071367
NID         g3265112
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 84)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
            Email: jonf@duke.edu.
FEATURES             Location/Qualifiers
     source          1..84
                     /organism="Caenorhabditis elegans"
                     /strain="N2"
                     /db_xref="taxon:6239"
                     /clone="VL10"
                     /clone_lib="mRNA from cadmium-responsive gene"
                     /tissue_type="whole animal"
                     /dev_stage="mixed population"
BASE COUNT       29 a    10 c    27 g    18 t
ORIGIN
        1 tagcaagtgc ggagacaaat gtgaatgcag tggagacaag tgttgtgaga agtactgctg
       61 tgaggattcc agtgagaaaa aatc
//

LOCUS       AF071366      217 bp   mRNA         EST    30-JUN-1998
DEFINITION  AF071366 mRNA from cadmium-responsive gene Caenorhabditis elegans
            cDNA clone VL1, mRNA sequence.
ACCESSION   AF071366
NID         g3265111
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 217)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display

Fig. 5A-29

```
        JOURNAL   Unpublished (1998)
        COMMENT
                Contact: Jonathan H. Freedman
                Nicholas School of the Environment
                Duke University
                Box 90328, Durham, NC 27708-0328, USA
                Email: jonf@duke.edu.
        FEATURES         Location/Qualifiers
             source       1..217
                         /organism="Caenorhabditis elegans"
                         /strain="N2"
                         /db_xref="taxon:6239"
                         /clone="VL1"
                         /clone_lib="mRNA from cadmium-responsive gene"
                         /tissue_type="whole animal"
                         /dev_stage="mixed population"
        BASE COUNT     69 a    37 c    67 g    44 t
        ORIGIN
            1 tagcaagtgc ggagacaaat gtgaatgcag tggagacaag tgttgtgaga agtactgctg
           61 tgaggaggcc agtgagaaaa aatgctgtcc agctggatgt aagggagact gcaagtgtgc
          121 aaactgtcat tgtgcagagc agaagcagtg cggagacaag acccatcaac accagggaac
          181 tgctgcggct cattaaaatg tttcagagtt gaatcta
        //

LOCUS       AF071365     292 bp    mRNA        EST     30-JUN-1998
        DEFINITION  AF071365 mRNA from cadmium-responsive gene Caenorhabditis elegans
                    cDNA clone DDRT22, mRNA sequence.
        ACCESSION   AF071365
        NID         g3265110
        KEYWORDS    EST.
        SOURCE      Caenorhabditis elegans.
          ORGANISM  Caenorhabditis elegans
                    Eukaryota; Metazoa; Nematoda; Secernentea; Rhabditia; Rhabditida;
                    Rhabditina; Rhabditoidea; Rhabditidae; Peloderinae; Caenorhabditis.
        REFERENCE   1  (bases 1 to 292)
          AUTHORS   Freedman,J.H. and Liao,H.-C.
          TITLE     Cadmium-Regulated Genes from the Nematode Caenorhabditis elegans.
                    Identification and cloning of new cadmium-responsive genes by
                    differential display
          JOURNAL   Unpublished (1998)
        COMMENT
                Contact: Jonathan H. Freedman
                Nicholas School of the Environment
                Duke University
                Box 90328, Durham, NC 27708-0328, USA
                Email: jonf@duke.edu.
        FEATURES         Location/Qualifiers
             source       1..292
                         /organism="Caenorhabditis elegans"
                         /strain="N2"
                         /db_xref="taxon:6239"
                         /clone="DDRT22"
                         /clone_lib="mRNA from cadmium-responsive gene"
                         /tissue_type="whole animal"
```

/dev_stage="mixed population"
BASE COUNT    101 a    60 c    50 g    81 t
ORIGIN

Fig. 5A-30

```
  1 tggtactcca cacggacaaa tacatttagt tttacaagcc gccacgcgac acgcaacgcc
 61 gtaaatctac caaggtacaa caacaacatg tcaagcacag acccatatct tatttgtgcg
121 gaacgagatg gcctctactg tagtaatcga caattggact cttatccacc ggatcactta
181 acctattttg atattaatat tcctattggg atcacagggt ttgcccgaaa atgtaattat
241 gaactgaatt gaaatgtatt ataaattagt ttttattggg aaaaaaaaaa aa
//
```

LOCUS       AF071364       188 bp    mRNA       EST       30-JUN-1998
DEFINITION  AF071364 mRNA from cadmium-responsive gene Caenorhabditis elegans
            cDNA clone DDRT21D, mRNA sequence.
ACCESSION   AF071364
NID         g3265109
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1 (bases 1 to 188)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
            Email: jonf@duke.edu.
FEATURES             Location/Qualifiers
     source          1..188
                     /organism="Caenorhabditis elegans"
                     /strain="N2"
                     /db_xref="taxon:6239"
                     /clone="DDRT21D"
                     /clone_lib="mRNA from cadmium-responsive gene"
                     /tissue_type="whole animal"
                     /dev_stage="mixed population"
BASE COUNT     44 a    31 c    51 g    62 t
ORIGIN 1 tataggttaa gtgatccggt ggataagagt ccaattgtcg attactacag tagaggccat
 61 ctgcttccgc acaaataaga tatgggtctg tgcttgacat gttgttgttg taccttgggt
121 agatttacgg cagttgcgtg tcgttggcgg cttgtaaaac taaatgtatt tttccgtgtg
181 gagtacca
//
```

LOCUS       AF071363       289 bp    mRNA       EST       30-JUN-1998
DEFINITION  AF071363 mRNA from cadmium-responsive gene Caenorhabditis elegans
            cDNA clone DDRT20, mRNA sequence.
ACCESSION   AF071363
NID         g3265108

Fig. 5A-31

```
KEYWORDS  EST.
SOURCE    Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE  1  (bases 1 to 289)
  AUTHORS  Freedman,J.H. and Liao,H.-C.
  TITLE    Cadmium-Regulated Genes from the Nematode Caenorhabditis elegans.
           Identification and cloning of new cadmium-responsive genes by
           differential display
  JOURNAL  Unpublished (1998)
COMMENT
           Contact: Jonathan H. Freedman
           Nicholas School of the Environment
           Duke University
           Box 90328, Durham, NC 27708-0328, USA
           Email: jonf@duke.edu.
FEATURES          Location/Qualifiers
     source       1..289
                  /organism="Caenorhabditis elegans"
                  /strain="N2"
                  /db_xref="taxon:6239"
                  /clone="DDRT20"
                  /clone_lib="mRNA from cadmium-responsive gene"
                  /tissue_type="whole animal"
                  /dev_stage="mixed population"
BASE COUNT       63 a    56 c    75 g    95 t
ORIGIN
        1 ttttttttt tttgtacat tatggcaaat ggaggcactg tctggttccg tggggtcatg
       61 gtgcattgga tcatggtata tcctatcctg gcttctaatc ccaatgcgtt tacagtcatg
      121 tgggcttgaa cgggcctagc tgagcttgga caaagttcct tgacagtacg ggtcgacaag
      181 cttgacagtc agaaattagg cacttgtggg ctacaggtgc tcgtaattat tttgagagtt
      241 ctgggcttcc ggactttac taggctaatc taagacaact gggctctaa
//
```

```
LOCUS       AF071362    214 bp    mRNA           EST        30-JUN-1998
DEFINITION  AF071362 mRNA from cadmium-responsive gene Caenorhabditis elegans
            cDNA clone DDRT2, mRNA sequence.
ACCESSION   AF071362
NID         g3265107
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE  1  (bases 1 to 214)
  AUTHORS  Freedman,J.H. and Liao,H.-C.
  TITLE    Cadmium-Regulated Genes from the Nematode Caenorhabditis elegans.
           Identification and cloning of new cadmium-responsive genes by
           differential display
  JOURNAL  Unpublished (1998)
COMMENT
           Contact: Jonathan H. Freedman
           Nicholas School of the Environment
```

Duke University
Box 90328, Durham, NC 27708-0328, USA
Email: jonf@duke.edu.

Fig. 5A-32

FEATURES         Location/Qualifiers
    source      1..214
                /organism="Caenorhabditis elegans"
                /strain="N2"
                /db_xref="taxon:6239"
                /clone="DDRT2"
                /clone_lib="mRNA from cadmium-responsive gene"
                /tissue_type="whole animal"
                /dev_stage="mixed population"
BASE COUNT     77 a    37 c    40 g    60 t
ORIGIN
      1 aaatcatggc ggcggatgca acagtcttct caattggcaa ctgtctatat cattccgcaa
     61 cacatttcgg atgttctcga aaaggacttc ccaaagttat tggagtactg tgaaagagtt
    121 cgtcatgaag tttcccaaag gacttttacta tgtgaattaa attgtcaaac tagtagtcag
    181 atcaataaaa ttttacgtgg aaaaaaaaaa aaaa
//

LOCUS       AF071361        322 bp    mRNA        EST        30-JUN-1998
DEFINITION  AF071361 mRNA from cadmium-responsive gene Caenorhabditis elegans
            cDNA clone DDRT19, mRNA sequence.
ACCESSION   AF071361
NID         g3265106
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 322)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
            Email: jonf@duke.edu.
FEATURES         Location/Qualifiers
    source      1..322
                /organism="Caenorhabditis elegans"
                /strain="N2"
                /db_xref="taxon:6239"
                /clone="DDRT19"
                /clone_lib="mRNA from cadmium-responsive gene"
                /tissue_type="whole animal"
                /dev_stage="mixed population"
BASE COUNT    102 a    77 c    70 g    73 t
ORIGIN
      1 taggtgaccg tagagaagcc cagatattta aaatctaaag ggaaactgtt tgaccagaag

*Fig. 5A-33*

```
 61 attagagccc agttgtctta gatagcctag taaaagtccg gaagcccaga actctcaaaa
121 taattacgag cacctgtagc ccacaagtgc ctaatttctg actgtcaagc ttgtcgaccc
181 gtactgtcaa ggaactttgt caagctcagc taggcccgtt caagcccaca tgactgtaaa
241 cgattcggga ttagaagcca ggataggata tccatgatcc aatgcaccat gacccacgga
301 accagatgtg ctcattacat ag
//
```

```
LOCUS       AF071360      228 bp    mRNA          EST       30-JUN-1998
DEFINITION  AF071360 mRNA from cadmium-responsive gene Caenorhabditis elegans
            cDNA clone DDRT18, mRNA sequence.
ACCESSION   AF071360
NID         g3265105
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 228)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
            Email: jonf@duke.edu.
FEATURES             Location/Qualifiers
     source          1..228
                     /organism="Caenorhabditis elegans"
                     /strain="N2"
                     /db_xref="taxon:6239"
                     /clone="DDRT18"
                     /clone_lib="mRNA from cadmium-responsive gene"
                     /tissue_type="whole animal"
                     /dev_stage="mixed population"
BASE COUNT      70 a     49 c     20 g     89 t
ORIGIN
    1 tttttttt tttccccatt catcacacac tatcatgttt tatattcaga cctattacct
   61 gtccagaaaa actgagctga aaaaatcccg gacgagcagc tccttcacat tcaaaatctt
  121 ccatcattc cccactcaat tcatttgttt tgtctttgat tttcaaattt tttgccttat
  181 tattttattg ctaaattaag aaaactgtta ctttgcaaaa aaaaaaaa
//
```

```
LOCUS       AF071359      255 bp    mRNA          EST       30-JUN-1998
DEFINITION  AF071359 mRNA from cadmium-responsive gene Caenorhabditis elegans
            cDNA clone DDRT1. mRNA sequence.
ACCESSION   AF071359
NID         g3265104
KEYWORDS    EST.
SOURCE      Caenorhabditis elegans.
  ORGANISM  Caenorhabditis elegans
```

Fig. 5A-34

```
         Eukaryota; Metazoa; Nematoda; Secernentea; Rhabditia; Rhabditida;
         Rhabditina; Rhabditoidea; Rhabditidae; Peloderinae; Caenorhabditis.
REFERENCE   1  (bases 1 to 255)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
            Email: jonf@duke.edu.
FEATURES            Location/Qualifiers
     source         1..255
                    /organism="Caenorhabditis elegans"
                    /strain="N2"
                    /db_xref="taxon:6239"
                    /clone="DDRT1"
                    /clone_lib="mRNA from cadmium-responsive gene"
                    /tissue_type="whole animal"
                    /dev_stage="mixed population"
BASE COUNT      113 a    25 c    51 g    66 t
ORIGIN
        1 atcattcaag aaagctatta tcagaaaaca taaatgacat agatcaagtg taaatcacat
       61 atatataaag tggataaata tatatagtta aacggataag gaaattaatt aatgaatttt
      121 gaaactggca gcgaaggatg aacagggaaa ggcacatgtt aaaataaatg aatgtgtata
      181 atttcgtgaa gagttagtta tgttaggtga tggcagccat gcagaatgag ccattgttcc
      241 gaaaaaaaaa aaaaa
//

LOCUS       AF071358      433 bp    mRNA            EST       30-JUN-1998
DEFINITION  AF071358 mRNA from cadmium-responsive gene Caenorhabditis elegans
            cDNA clone DDRT17, mRNA sequence.
ACCESSION   AF071358
NID         g3265103
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 433)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
            Email: jonf@duke.edu.
```

Fig. 5A-35

```
FEATURES         Location/Qualifiers
     source      1..433
                 /organism="Caenorhabditis elegans"
                 /strain="N2"
                 /db_xref="taxon:6239"
                 /clone="DDRT17"
                 /clone_lib="mRNA from cadmium-responsive gene"
                 /tissue_type="whole animal"
                 /dev_stage="mixed population"
BASE COUNT      149 a    63 c    83 g   138 t
ORIGIN
    1 tggtactaag ggccaataac tgagcttttg cacggcggca tcaatgataa agagaaacta
   61 ttttgacgg ttaaaataac caaatttaca ccggcgagtc aatcaaaaat tctcatctgg
  121 aacagcaaag tacatcggag aattgctgga aggaagcact gatgaaacta aattaactgc
  181 tggatgcata ggaaaaacgt caagattgac gtggagttgg agagaaggac tatgtttgga
  241 tggttactaa gattttgtaa ctggtgacaa taaggacatc acttttctaa ctaacttaaa
  301 ttcttttta cttcttttct tctgaattaa ttgtgtttta aggcgaattc tatgtttcag
  361 aatttattta cgtttgcttt ttcatgttta attgtaaaag taagcaattt ttccaccgta
  421 aaaaaaaaaa aaa
//

LOCUS       AF071357      933 bp     mRNA        EST      30-JUN-1998
DEFINITION  AF071357 mRNA from cadmium-responsive gene Caenorhabditis elegans
            cDNA clone DDRT16FC, mRNA sequence.
ACCESSION   AF071357
NID         g3265102
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 933)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT     Contact: Jonathan H. Freedman
            Nicholas School of the Environment
            Duke University
            Box 90328, Durham, NC 27708-0328, USA
            Email: jonf@duke.edu.
FEATURES         Location/Qualifiers
     source      1..933
                 /organism="Caenorhabditis elegans"
                 /strain="N2"
                 /db_xref="taxon:6239"
                 /clone="DDRT16FC"
                 /clone_lib="mRNA from cadmium-responsive gene"
                 /tissue_type="whole animal"
                 /dev_stage="mixed population"
BASE COUNT      275 a   190 c   171 g   297 t
ORIGIN
```

Fig. 5A-36

```
  1 catgcatctt tttttttt tttttttta ctgtctcaag tatgttggat tcatgtttga
 61 ttattactgc tgcgctgttt ggagccgctg tcatttactt gaaaaatttc ttcactgttc
121 ctagcattaa accaaaacct gatattcaca aaaaagacta caaaaaggat gtagtctatc
181 tgtatcagat gaagagactc aagaactgtc cgaacttgtc ccctttctgc atgaaaatcg
241 agattctttg tagaatcttc aagattcctt acgagattat cacatgcacc tctgaacgct
301 ctcggaatgg attggtccct ttcgttgaac tcaatggaga gcacattgct gattctgatc
361 ttatcgaaat gcgcttgaga tcacatttta aaattccgtc gcttccaact gagctggaaa
421 ctcaatctgt tgctctaagc aagtttgcag atcaccattt gttcttcgta cttatacgat
481 ttaaaattgc tgtcgacgaa ttctacaaaa ccattatcga aataatcggt ctcccaacct
541 tcctgaattt ccttctcatg cccctttga aggctataat cgggaaaaat gtctacaaca
601 aatgtcaggg agccattgga gatttgaat tgagtgagct cgacgagatt cttcacagag
661 atttgcgaat cgtagagaac accttggcca agaaaaagtt tcttttcggg gaggaaatca
721 cggcggcgga tgcaacagtc ttctctcaat tggcaactgt ctattatcca ttccgcaatc
781 acatttcgga tgttctcgaa aaggacttcc caaagttatt ggagtactgt gaaagagttc
841 gtcatgaagt ttacccaaag gactttacta tgtgaattaa attgtcaaac tagtagtcag
901 atcaataaaa ttctacgtgg caaaaaaaaa aaa
//
```

LOCUS       AF071356      238 bp    mRNA         EST       30-JUN-1998
DEFINITION  AF071356 mRNA from cadmium-responsive gene Caenorhabditis elegans
            cDNA clone DDRT16, mRNA sequence.
ACCESSION   AF071356
NID         g3265101
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 238)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
            Email: jonf@duke.edu.
FEATURES             Location/Qualifiers
     source          1..238
                     /organism="Caenorhabditis elegans"
                     /strain="N2"
                     /db_xref="taxon:6239"
                     /clone="DDRT16"
                     /clone_lib="mRNA from cadmium-responsive gene"
                     /tissue_type="whole animal"
                     /dev_stage="mixed population"
BASE COUNT      77 a     42 c     45 g     74 t
ORIGIN
  1 tttttttt tttgggagga aatcacggcg gcggatgcaa cagtcttctc tcaattggca
 61 actgtctatt atccattccg caatcacatt tcggatgttc tcgaaaagga cttcccaaag
121 ttattggagt actgtgaaag agttcgtcat gaagtttacc caaaggactt tactatgtga
```

Fig. 5A-37

```
    181 attaaattgt caaactagta gtcagatcaa taaaattcta cgtggcaaaa aaaaaaaa
//

LOCUS       AF071355       248 bp    mRNA        EST       30-JUN-1998
DEFINITION  AF071355 mRNA from cadmium-responsive gene Caenorhabditis elegans
            cDNA clone DDRT15, mRNA sequence.
ACCESSION   AF071355
NID         g3265100
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 248)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
            Contact: Jonathan H. Freedman
            Nicholas School of the Environment
            Duke University
            Box 90328, Durham, NC 27708-0328, USA
            Email: jonf@duke.edu.
FEATURES             Location/Qualifiers
     source          1..248
                     /organism="Caenorhabditis elegans"
                     /strain="N2"
                     /db_xref="taxon:6239"
                     /clone="DDRT15"
                     /clone_lib="mRNA from cadmium-responsive gene"
                     /tissue_type="whole animal"
                     /dev_stage="mixed population"
BASE COUNT       67 a     46 c     31 g    104 t
ORIGIN
      1 tttttttt ttcgcatgt tgtaatacta atatttatta attttcttta attttctttg
     61 ttaagtttgt atttataggt tgttgagatt ttttgcctg taattttgca actgtgattc
    121 atgtatgtac tatatgaacc gaaacccct cccgtcatac acaacagtta gtaaaacatt
    181 ttaatcccat atttctcatt cccaacactc ttacaggttt tgcatcagca gcagcagtgc
    241 aaacacaa
//

LOCUS       AF071354       226 bp    mRNA        EST       30-JUN-1998
DEFINITION  AF071354 mRNA from cadmium-responsive gene Caenorhabditis elegans
            cDNA clone DDRT12, mRNA sequence.
ACCESSION   AF071354
NID         g3265099
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1  (bases 1 to 226)
```

Fig. 5A-38

```
     AUTHORS   Freedman,J.H. and Liao,H.-C.
     TITLE     Cadmium-Regulated Genes from the Nematode Caenorhabditis elegans.
               Identification and cloning of new cadmium-responsive genes by
               differential display
     JOURNAL   Unpublished (1998)
COMMENT
          Contact: Jonathan H. Freedman
          Nicholas School of the Environment
          Duke University
          Box 90328, Durham, NC 27708-0328, USA
          Email: jonf@duke.edu.
FEATURES             Location/Qualifiers
     source          1..226
                     /organism="Caenorhabditis elegans"
                     /strain="N2"
                     /db_xref="taxon:6239"
                     /clone="DDRT12"
                     /clone_lib="mRNA from cadmium-responsive gene"
                     /tissue_type="whole animal"
                     /dev_stage="mixed population"
BASE COUNT      68 a     38 c     35 g     85 t
ORIGIN
        1 tttttttt tttgtaaca aagaactgag cactctatgg tttatcaagt ctatatgtat
       61 ccgtgatgcc tactgtatcg tacatccatc tcgatcgtaa tgcattattg atcatgagtt
      121 cccaaaggtc ttaatcttga caaaggtgca atagatatat atccttattt ggcactatat
      181 atatgttcag aattatgact gatcgataca tatgatcaaa gttaca
//

LOCUS       AF071353      212 bp    mRNA         EST       30-JUN-1998
DEFINITION  AF071353 mRNA from cadmium-responsive gene Caenorhabditis elegans
            cDNA clone DDRT10. mRNA sequence.
ACCESSION   AF071353
NID         g3265098
KEYWORDS    EST.
SOURCE      Caenorhabditis elegans.
  ORGANISM  Caenorhabditis elegans
            Eukaryota; Metazoa; Nematoda; Secernentea; Rhabditia; Rhabditida;
            Rhabditina; Rhabditoidea; Rhabditidae; Peloderinae; Caenorhabditis.
REFERENCE   1 (bases 1 to 212)
  AUTHORS   Freedman,J.H. and Liao,H.-C.
  TITLE     Cadmium-Regulated Genes from the Nematode Caenorhabditis elegans.
            Identification and cloning of new cadmium-responsive genes by
            differential display
  JOURNAL   Unpublished (1998)
COMMENT
          Contact: Jonathan H. Freedman
          Nicholas School of the Environment
          Duke University
          Box 90328, Durham, NC 27708-0328, USA
          Email: jonf@duke.edu.
FEATURES             Location/Qualifiers
     source          1..212
                     /organism="Caenorhabditis elegans"
                     /strain="N2"
```

Fig. 5A-39

```
            /db_xref="taxon:6239"
            /clone="DDRT10"
            /clone_lib="mRNA from cadmium-responsive gene"
            /tissue_type="whole animal"
            /dev_stage="mixed population"
BASE COUNT      68 a    35 c    34 g    75 t
ORIGIN
       1 ttcgatacag gaactacatt tacatctgtt tcaacatatc aacaatacat aacatactca
      61 atccttcagg ctctgaagga ttttgagtgc gatatactgt aacaagctcg ggaaacataa
     121 gtacattttt tggagctatc tttttatgtt gcgcttttct tttgtctctt tgaatgagtt
     181 ttgaaatgaa ttgtctgtgc aaaaaaaaaa aa
//
```

STRESSOR REGULATED GENES

This application claims the benefit of U.S. provisional No. 60/109,281, filed Nov. 20, 1998.

This invention was made with Government support under Grant No. ES01908 awarded by the National Institutes of Health. The Government has certain rights in the invention.

TECHNICAL FIELD

The present invention relates, in general, to stressor-responsive genes and, in particular, to metal-responsive genes, to mRNAs, to proteins encoded therein and to uses thereof, for example, as biomonitors and in drug discovery.

BACKGROUND

The transition metal cadmium is considered to be a serious occupational and environmental toxin. Cadmium was ranked number 7 on the Agency for Toxic Substances and Disease Registry/Environmental Protection Agency "Top 20 Hazardous Substances Priority List" in 1997 (Fay et al. (1997) Food Chem. Toxicol. 34, 1163–1165). In addition, it is a frequently found contaminant at Superfund sites (Fay et al. (1997) Food Chem. Toxicol. 34, 1163–1165). Cadmium is used primarily in metal coatings, nickel-cadmium batteries and pigments (Friberg et al. (1986) in Handbook of the Toxicology of Metals (Friberg, L, Nordberg G. F. and Vouk, V., ed) pp. 130–237, Elsevier/North-Holland, Amsterdam; Aylett, B. J. (1979) in The Chemistry, Biochemistry and Biology of Cadmium (Webb, M., ed) pp. 1, Elsevier/North-Holland, New York). It is also continuously introduced into the atmosphere through the smelting of ores and the burning of fossil fuels (Friberg et al. (1986) in Handbook of the Toxicology of Metals (Friberg, L, Nordberg G. F. and Vouk, V., ed) pp. 130–237, Elsevier/North-Holland, Amsterdam; Aylett, B. J. (1979) in The Chemistry, Biochemistry and Biology of Cadmium (Webb, M., ed) pp. 1, Elsevier/North-Holland, New York). It has been suggested that increased industrialization has resulted in higher levels of accumulated cadmium in humans (Fortoul et al. (1996) Environ. Health Perspect. 104, 630–632). The primary routes of non-occupational exposure in humans are via inhalation, and ingestion of cadmium-containing food (Waalkes et al. (1992) Crit. Rev. Toxicol. 22, 175–201). Humans are continuously exposed to cadmium and accumulate the metal throughout their lives in liver, lung and kidney tissue (Aylett, B. J. (1979) in The Chemistry, Biochemistry and Biology of Cadmium (Webb, M., ed) pp. 1, Elsevier/North-Holland, New York; Bernard et al. (1986) Experientia Suppl. 50, 114–123). Toxicological responses of cadmium exposure include kidney damage, respiratory diseases, such as emphysema and neurologic disorders (Waalkes et al. (1992) Crit. Rev. Toxicol. 22, 175–201; Chmielnicka et al. (1986) Biol. Trace Elemants Res. 10, 243–256). Cadmium has been classified as a type 1 human carcinogen (Internation Agency for Research on Cancer (1993) Beryllium, Cadmium, Mercury and Exposures in the Glass Manufacturing Industry, Vol. 58, IARC, Lyon). It induces site of exposure, lung, kidney, prostate and testicular cancers in rats and mice (Waalkes et al. (1992) Crit. Rev. Toxicol. 22, 175–201). Human epidemiological data suggests that it causes tumors of the male reproductive system and induces respiratory tumors (Waalkes et al. (1992) Crit. Rev. Toxicol. 22, 175–201; Oberdorster, G. (1986) Scand. J. Work Environ. Health 12, 523–537).

Intracellular damage associated with cadmium exposure includes protein denaturation, lipid peroxidation and DNA strand breaks. Proposed mechanisms by which cadmium induces this damage involve (a) metal binding to reduced cysteine residues and (b) the generation of reactive oxygen species, possibly by lowering reduced glutathione levels (Abe, T. et al. (1994) Biochim. Biophys. Acta. 1201, 29–36;Manca, D. et al. (1991)Toxicology 67, 303–323; Chin, T. A. et al. (1993) Toxicology 77, 145–156). To prevent cadmium-induced intracellular damage, cells respond to metal exposure by inducing the transcription of genes that encode defense and repair proteins. These proteins (a) chelate the metal to prevent further damage, (b) remove reactive oxygen species, (c) repair membrane and DNA damage and (d) renature or degrade unfolded-proteins. Cadmium has been shown to affect the steady-state levels of the mRNAs encoding metallothionein (Hamer, D. H. (1986) Annu. Rev. Biochem. 55, 913–951), heme oxygenase (Adam, J. et al. (1989) J. Biol. Chem. 264, 6371–6375), γ-glutamylcysteine synthetase (Hatcher. E. L. et al. (1995) Free Radic. Biol. Med. 19, 805–812), low and high molecular weight heat shock proteins (Wiegant. F. A. et al. (1994) Toxicology 94, 143–159) and ubiquitin (Muller-Taubenberger, A. et al. (1988) J. Cell Sci. 90, 51–58). In addition, increases in superoxide dismutase, catalase, glutathione peroxidase and glucose-6-phosphate dehydrogenase activities are observed following cadmium exposure in cultured cells and whole animals (Kostic, M. M. et al. (1993). Eur. J. Haematol. 51, 86–92; Salovsky P. et al. (1992) Hum. Exp. Toxicol. 11, 217–222). The mechanism(s) by which this metal modulates the levels of expression of most of these genes remains unknown.

Cadmium-activated transcription may occur through specific metal-responsive upstream regulatory elements found in the promoters of cadmium-responsive genes. These may include metal responsive element (MRE) sequences, found in most metallothionein genes (Stuart, G. W. et al. (1984) Proc. Natl. Acad. Sci. USA 81, 7381–7322; Searle, P. F. (1990) Nucleic Acids Res. 18, 4863–4690; Cizewski Culotta, V. C. et al. (1989) Mol. Cell. Biol. 9, 1376–1380), or cadmium-responsive elements, as found in the human heme oxygenase gene (Takeda, K. et al. (1994) J. Biol. Chem. 265, 14061–14064). Cadmium may also affect gene expression by influencing signal transduction pathways. Cadmium affects the activities of PKC, PKA and calmodulin (Wang, Z. et al. (1998) J. Biol. Chem. 273, 73–79; Beyersmann, D. et al. (1997) Toxicol. Appl. Pharmacol. 144, 247–261). It has been suggested that cadmium-induced transcription of the proto-oncogenes jun and fos is mediated via PKC and calmodulin (Wang, Z. et al. (1998) J. Biol. Chem. 273, 73–79). Thus, cadmium can modulate the activities of complex signal transduction pathways that in turn can influence the expression of a myriad of genes. However, relatively few cadmium-responsive genes have been identified. In addition, there is a paucity of information on the influence of cell-specific and developmental factors on metal-inducible gene expression.

SUMMARY OF THE INVENTION

The present invention relates to stressor-regulated genes in general and specifically to metal-regulated genes, such as cadmium-regulated genes, mRNAs and to the proteins encoded therein. The invention also relates to the use of such genes and proteins as biomonitors and in drug discovery.

Objects and advantages of the present invention will be clear from the description that follows.

elegans (−) and nematodes exposed to 100 μM CdCl$_2$ for 24 h (+) and 20 μg was then subjected to denaturing gel electrophoresis. Northern blots were hybridized with a $^{32}$P-labeled oligonucleotide probe that is specific for mtl-2mRNA; nt 182–221 (upper panel) (Freedman, J. H. et al. (1993) *J. Biol. Chem.* 268, 2554–2564). Following autoradiography, the labeled probe was removed and the membrane reprobed with a $^{32}$P-labeled DNA probe specific for the myosin light-chain mRNA (lower panel). There are two forms of *C. elegans* myosin light-chain mRNA, containing 900 and 1300 nt (Freedman, J. H. et al. (1993) *J. Biol. Chem.* 268, 2554–2564; Cummins, C. et al. (1988) *Mol. Cell. Biol* 8, 5334–5349).

Figures 2A, 2B:
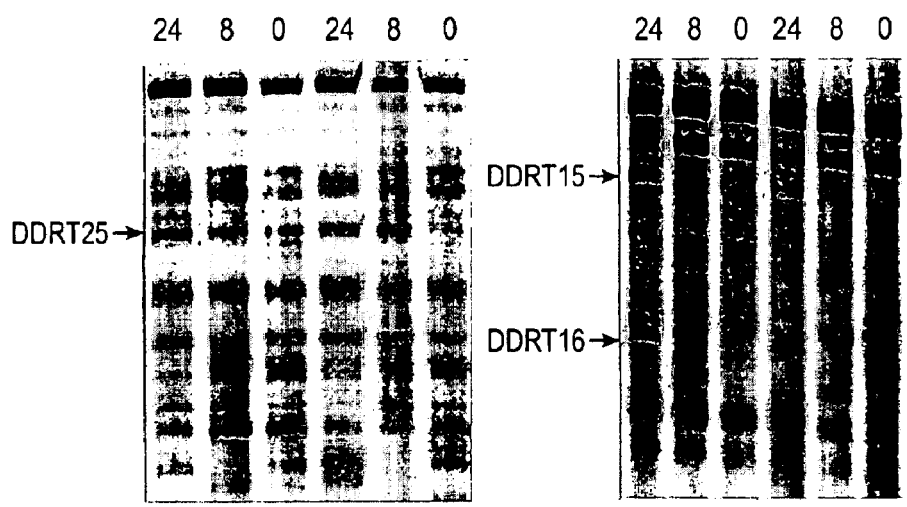

FIGS. 2A and 2B. Representative mRNA differential display band patterns of control and cadmium-treated *C. elegans*. Total RNA was isolated from *C. elegans* exposed to cadmium for 0, 8 and 24 h and analyzed by differential display. RNA from duplicate populations of treated and control *C. elegans* was reverse transcribed and amplified with the 3′-degenerate anchored oligo(dT) primer T$_{12}$MA and the 5′-arbitrary decamer AP-13 (FIG. 2A) and T$_{12}$MG and RT-10 (FIG. 2B). Amplified cDNA fragments were resolved by electrophoresis in a 6% denaturing polyacrylamide gel. cDNA fragments that were subsequently isolated (DDRT15, DDRT16 and DDRT25) are indicated by arrows.

Figures 3A, 3B:
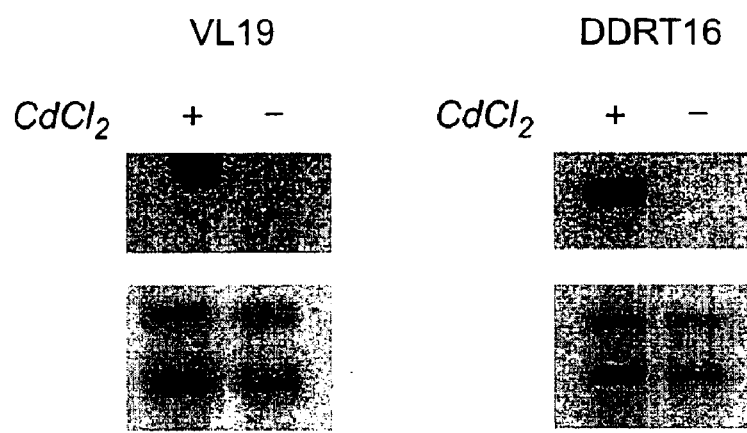

FIGS. 3A and 3B. Northern blot analysis showing differential expression of selected cadmium-responsive genes. *C. elegans* poly(A$^+$) RNA (2 μg), isolated from nematodes exposed to 100 μM CdCl$_2$ for 24 h (+) or control nematodes (−), was resolved by denaturing agarose gel electrophoresis. Northern blots were hybridized with $^{32}$P-labeled cDNA probes prepared from the differential display cDNA fragments VL19 (upper panel FIG. 3A) or DDRT16 (upper panel FIG. 3B). Following PhosphorImager analysis, the probes were removed and the membrane reprobed with a $^{32}$P-labeled DNA fragment homologous to myosin light-chain mRNAs (lower panels FIGS. 3A and 3B).

Figure 4A:
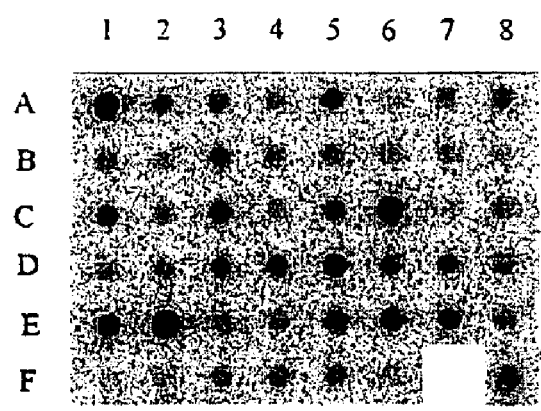
Figure 4B:
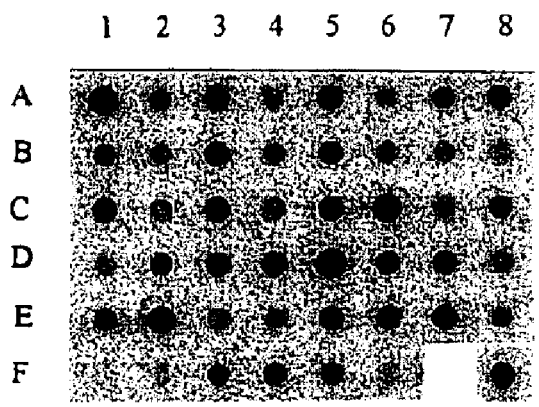
Figure 4C:
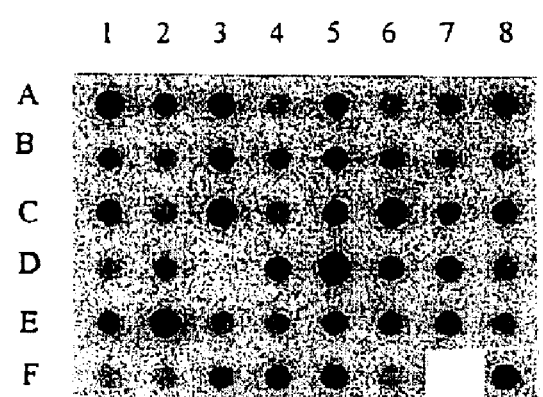

FIGS. 4A–4C. Representative reverse-Northern dot blot of differentially expressed genes. Cloned DNA fragments were amplified and ~100 ng of the amplified product was immobilized on triplicate membranes. The membranes were then hybridized with $^{32}$P-labeled cDNAs synthesized from poly(A$^+$) RNA prepared from either untreated *C. elegans* (FIG. 4A), or those exposed to cadmium for 8 h (FIG. 4B) or 24 h (FIG. 4C). The location of each differentially expressed DNA fragment, and the myosin light-chain (MLC) and metallothionein (MTL-1) controls, on the blots is presented in the following grid legend:

41, 40, 38, 36, 35, 33, 44, 32, 31, 20, 16, 15, 14, 13, 12, 10, 19, 9, 8, 7, 6, 5, 18, 3, 2, 1, 17, 30, 22, 21, 46, 45, 21, 29, 28, 48, 27, 47, 26, 25, 24, respectively.

DETAILED DESCRIPTION OF THE INVENTION

The present invention results, at least in part, from the realization that the non-parasitic nematode *Caenorhabditis elegans* provides an excellent model system for obtaining an integrated picture of cellular, developmental and molecular aspects of the regulation of metal-responsive gene expression (e.g., transition and heavy metal responsive gene expression, including, cadmium, mercury, copper, zinc, nickel, lead, chromium, and silver responsive gene expression). The adult hermaphrodite is composed of 959 somatic cells, but contains highly differentiated muscle, nervous, digestive and reproductive systems (Sulstion, J. (1988) in *The Nematode Caenorhabditis elegans* (Wood, W. B., ed) pp. 123–155, Cold Spring Harbor Laboratory Press, Cold Spring Harbor, N.Y.; Kenyon, C. (1988) *Science* 240, 1448–1453). The developmental and cellular biology of *C. elegans* is thoroughly understood in exceptional detail (Sulstion, J. (1988) in *The Nematode Caenorhabditis elegans* (Wood, W. B., ed) pp. 123–155, Cold Spring Harbor Laboratory Press, Cold Spring Harbor, N.Y.; Kenyon, C. (1988) *Science* 240, 1448–1453). High levels of evolutionary conservation between *C. elegans* and higher organisms are observed in many signal transduction, gene regulatory and developmental pathways (McGhee, J. D. et al. (1997) in *C. elegans* II (Riddle, D. L., Blumenthal, T., Meyer, B. J. and Priess, J. R., eds) pp. 147–184, Cold Spring Harbor Laboratory Press, Cold Spring Harbor, N.Y.; Han, M. et al. (1990) *Cell* 65, 921–931; Clark, S. G. et al. (1992) *Nature* 356, 340–344). In addition, homologues of many of the proteins induced as part of metal-activated stress-responses in vertebrates have been identified in *C. elegans*. These include metallothionein (Slice, L. W. et al. (1990) *J. Biol. Chem.* 265, 256–263; Freedman, J. H. et al. (1993) *J. Biol. Chem.* 268, 2554–2564), superoxide dismutase (Giglio, A. M. et al. (1994) *Biochem. Mol. Biol. Int.* 33, 41–44; Giglio, M. P. et al. (1994) *Biochem. Mol. Biol. Int.* 33, 37–40), ubiquitin (Zhen, M. et al. (1993) *Mol. Cell. Biol.* 13, 1371–1377; Stringham, E. G. et al. (1992) *Gene* 113, 165–173), heat shock protein 70 (Heschl, M. F. P. et al. (1989) *DNA* 8, 233–243), glutathione-S-transferase (Weston, K. et al. (1989) *Nucleic Acids Res.* 17, 2138–2139) and catalase (Ebert, R. H. et al. (1996) *Dev. Genet.* 18, 131–143). With the exception of metallothionein, the effect of cadmium on the transcription of these *C. elegans* genes remains

|     | Column |         |         |        |         |         |        |        |
| --- | ------ | ------- | ------- | ------ | ------- | ------- | ------ | ------ |
| Row | 1      | 2       | 3       | 4      | 5       | 6       | 7      | 8      |
| A   | MLC    | DDRT1   | DDRT2   | DDRT3  | DDRT4   | DDRT5   | DDRT6  | DDRT7  |
| B   | DDRT9  | DDRT10  | DDRT12  | DDRT15 | DDRT16  | DDRT17  | DDRT18 | DDRT19 |
| C   | DDRT20 | DDRT21U | DDRT21D | DDRT22 | DDRT23  | DDRT24  | DDRT25 | DDRT26 |
| D   | DDRT28 | DDRT29  | DDRT30  | DDRT32 | DDRT33U | DDRT33D | DDRT34 | DDRT35 |
| E   | DDRT36 | DDRT37  | DDRT38  | DDRT40 | DDRT41  | DDRT47  | DDRT48 | DDRT50 |
| F   | VL3    | VL9     | VL11    | VL19   | VL20    | VL21    |        | MTL-1  |

FIGS. 5A-1 to 5A-39. Sequences corresponding to GenBank Accession Nos. shown in Table III. Sequences shown in FIG. 5 correspond to SEQ ID NOs:44–52 and SEQ ID NOs:1–43, respectively. Sequences shown in Table III correspond to SEQ ID NOs:37, 34, 11, 4, 52, 51, 50, 49, 43, 42, unknown. *C. elegans* also contains homologues to many of the signal transduction proteins that have been implicated in modulating the cellular/molecular response to metal exposure (Gross R. E. et al. (1990) *J. Biol. Chem.* 265, 6896–6907; Lu, X-Y. et al. (1990) *J. Biol. Chem.* 265, 3293–3303; Land, M. et al. (1994) *J. Biol. Chem.* 269, 14820–14827; Land, M. et al. (1994) *J. Biol. Chem.* 269, 9234–9244).

One of the major advantages in using *C. elegans* as a model system, for example, to identify new metal-responsive genes, is the magnitude of cDNA and genomic DNA sequence data currently available. The nematode genome is relatively small (~$10^8$ bp), and an abundance of information is available on the genetic and physical maps of its chromosomes (Waterston, R. H. et al. in *C. elegans* II (Riddle, D. L., Blumenthal, T., Meyer, B. J. and Priess, J. R., eds) pp. 23–46, Cold Spring Harbor Laboratory Press, Cold Spring Harbor, N.Y.). Currently, sequencing of the entire *C. elegans* genome is >80% completed and >50,000 ESTs have been cloned and sequenced. Megabases of genomic and cDNA sequence data are readily available through GenBank, the *C. elegans* Genome Project (Coulson, A. (1996) *Biochem. Soc. Trans.* 24, 289–291) and the *C. elegans* cDNA Sequencing Project (Sequence data and information about the *C. elegans* DNA Project can be obtained at http colon forward slash forward slash www dot ddbj dot nig dot ac dot jp forward slash c hyphen elegans forward slash html forward slash CE underscore INDEXZ dot html forward slash).

As described in the Examples that follow, fifty-three differentially expressed DNA fragments from a mixed-stage population (i.e., a population at all stages of development) of cadmium-exposed *C. elegans* have been identified. Subsequent analysis confirms that the steady-state level of expression of forty-eight of these clones increases 2–6-fold following cadmium exposure. In addition, a single clone was isolated the level of expression of which decreased ~2-fold. Sequence analysis has identified *C. elegans* cosmids, predicted structural genes and ESTs that are identical to the differentially expressed mRNAs. Furthermore, the cadmium-responsive cDNAs are the products of thirty-two independent genes.

With the information provided in the Examples, three types of products, each of which is within the scope of the invention, can be directly obtained:

1. *C. elegans* genes the transcription of which is modulated by cadmium,

2. *C. elegans* mRNAs that are encoded by such genes, and

3. *C. elegans* proteins the expression of which may be affected by cadmium, and subsequently antibodies to these proteins (monoclonal or polyclonal, and antigen binding fragments thereof). These proteins can be expected to function in cadmium detoxification and/or the repair of intra- and intercellular damage.

Based on the BLAST sequence analysis provided in the Examples, the *C. elegans* cadmium-responsive genes can be divided into three categories:

1. *C. elegans* genes that encode proteins that have been shown to be responsive to cadmium in mammals (e.g., metallothionein, pyruvate carboxylase and heat-shock protein-70);

2. *C. elegans* genes for which mammalian homologues have been identified, but the mammalian genes, etc. have not been shown to be affected by cadmium (e.g., DNA gyrase collagen, human hypothetical protein KIAA0174 [this protein in evolutionarily conserved, it is found in rats and mice] and β-adrenergic receptor kinase); and 3. *C. elegans* genes that encode novel proteins (these predicted proteins do not have any significant homology to any protein currently in the database (e.g., DDRT16)).

Human homologues of proteins in the first two categories can be obtained easily. Using the mRNAs, gene fragments and antibodies derived from the *C. elegans* cadmium-responsive genes in the third category, homologues in higher organisms (e.g., mammals, including rates, mice and humans) of the mRNAs, genes and proteins can be obtained.

While specific reference is made in the Examples that follow to cadmium-toxicity, cadmium-response, etc., for purposes of the present invention, cadmium is functioning as an archetypical stressor. The effects seen with cadmium can be expected to occur with other transition and heavy metals (see above). In addition, other classes of chemical toxins (e.g., chemical carcinogens, oxidizing agents, polyaromatic hydrocarbons) and physical stresses (e.g., ultra-violet light, ionizing radiation, heat-shock, osmotic stress, and infectious agents), can affect the expression of these genes. Accordingly, it will be appreciated that the embodiments of the invention described below encompass stressors in addition cadmium.

Biomonitors

The invention includes within its scope biomonitor kits that can contain primers that can be used to amplify specific cadmium-responsive mRNAs in PCRs, or sequence-specific oligonucleotides for Northern blot and Rnase protection assays. Such kits can also contain antibodies specific for the responsive proteins. The kits can be used to assay levels of protein using, for example, Western blot or ELISA assays.

In accordance with this embodiment, the presence of cadmium responsive mRNAs can be determined and the levels of expression of the cadmium-responsive mRNAs or proteins measured in nematodes, indigenous species or humans in potentially contaminated environments to determine if exposure to cadmium has occurred.

In addition, the effectiveness of different therapies used to treat exposure to metals or other chemical toxins can be monitored (i.e., a diagnostic tool for measuring toxicity or stress). If the expression of these genes is found to be associated with disease states, then by monitoring the levels of the protein or mRNA the progression or remission of the disease can be followed. Further, if the expression of the cadmium-responsive genes is modulated by chemotherapeutic agents, as occurs with heat shock proteins and metallothionein, then the affect of these agents on the tumor and the patient can be monitored.

Transgenic Organisms (Plants and Animals)

The invention also includes within its scope *C. elegans* or other organisms, the genome of which has been engineered to include a cadmium-responsive gene. The gene can be modified to express a reporter protein (e.g., β-galactosidase or green fluorescent protein) in place of the normal structural gene. These organisms can be exposed to potentially contaminated environmental samples, water or dirt. The level of reporter gene expression will be proportional to the amount of contamination in the sample. These organisms, which themselves are biomonitors, can be used to measure the levels of bioavailable cadmium and determine the effectiveness of clean-up efforts.

It is expected that certain of the cadmium-responsive genes encode proteins that function in the detoxification and repair of cadmium-induced cellular damage. Over-expression of these proteins would result in the organism being resistant to metal toxicity. Transgenic plants that express the *C. elegans* cadmium-responsive proteins can be generated by controlling the expression the cadmium-responsive mRNA using plant or bacterial promoters. Plants that express these proteins can be expected to be resistant to metal toxicity and thus able to grow in contaminated environments.

There is the potential that disruption of one or more of the cadmium-responsive genes in mammals (i.e., preventing the expression of the native/functional protein) could mimic a human disease state. For example, disruption of VL19 (pyruvate carboxylase) may mimic a liver disease. A transgenic organism that functions as a disease model constitutes an important tool in the pharmaceutical and medical industries.

Drug Discovery

The ability to monitor the levels of expression of the cadmium-responsive proteins can be used in drug discovery. Drugs that modulate the expression of these proteins in humans can be expected to function as modulators of other forms of stress. Chemicals or drugs that can be used to increase the expression of the cadmium-responsive proteins can be expected to protect the organism from other stresses. (For example, a drug that increases the expression of one or more of the cadmium responsive genes may allow a patient to receive a higher dose of a chemotherapeutic drug.) A drug that inhibits the ability of cadmium to induce the expression of the mammalian homologues of the $C.$ $elegans$ genes can be expected to function in the prevention of cadmium toxicity or other stress-induced toxicities.

The invention includes within its scope drugs discovered using the methods described herein.

Pathways

The ability of cadmium to induce the transcription of the $C.$ $elegans$ genes is likely to be the result of the metal activating intracellular signaling pathways. These pathways ultimately activate transcription factors, which interact with the cadmium-responsive genes. For example, cadmium is taken up by the cell, it then binds to an intracellular receptor, this binding activates a series of protein phosphorylations and dephosphorylations and in the end the cadmium responsive gene is "turned-on." It is known that cadmium is a mammalian carcinogen and teratogen. However, the mechanisms that control these effects have not been discovered. A pathway that regulates the expression of the cadmium-responsive genes may represent new a pathway for the development of tumors or other disease. It may also define new pathways that control cell growth and differentiation.

Cadmium-responsive mRNA and protein probes that can be used in the identification of these pathways are within the scope of the invention. Such mRNA and protein probes can be used to monitor the effectiveness of drugs that interact with components of these pathways.

The non-limiting Examples that follow describe certain aspects of the invention in greater detail.

EXAMPLES

The following experimental details are referenced in the specific Examples that follow.

Growth and isolation of $C.$ $elegans$—The N2 strain of $C.$ $elegans$ was grown in liquid S medium (0.1M NaCl, 50 mM potassium phosphate, pH 6.0, 5 $\mu$g/ml cholesterol, 10 mM potassium citrate, 3 mM $CaCl_2$, 3 mM $MgCl_2$, 50 $\mu$M EDTA, 25 $\mu$M $FeSO_4$, 10 $\mu$M $MnCl_2$, 10 $\mu$M $ZnSO_4$ and 1 $\mu$M $CuSO_4$) using $E.$ $coli$ OP50 as a food source (Brenner, S. (1974) $Genetics$ 77, 71–94). In experiments where nematodes were exposed to cadmium, the medium was supplemented with 100 $\mu$M $CdCl_2$ (Freedman, J. H. et al. (1993) $J.$ $Biol.$ $Chem.$ 268, 2554–2564). $C.$ $elegans$ were grown in the presence of metal for 8 h or 24 h at ~20° C. Nematodes were then collected following centrifugation at 800×g for 5 min. Pellets were suspended in 5 mM NaCl containing 35% sucrose (final concentration) and viable nematodes were collected from the top of the solution following centrifugation at 1000×g for 5 min at 4° C. Nematodes were then washed three times by suspension in M9 buffer (22 mM $KH_2PO_4$, 42 mM $Na_2HPO_4$, 85 mM NaCl, 1 mM $MgSO_4$) followed by sedimentation at 800×g. Washed nematode pellets were finally suspended in a small volume of M9 buffer, rapidly frozen in liquid nitrogen and stored at –80° C.

RNA isolation—Total RNA was isolated from mix-stage populations of $C.$ $elegans$ exposed to 100 $\mu$M $CdCl_2$ for 8 h and 24 h and control, non-exposed nematodes. Frozen worms were first ground into a fine powder using a liquid nitrogen-cooled mortar and pestle. Powdered $C.$ $elegans$ (200 mg) were then homogenized in 2 ml of TRIzol (GIBCO/BRL). RNA was then collected from the aqueous phase following the addition of chloroform, precipitated by adding isopropyl alcohol and then air-dried. The dried RNA pellet was then dissolved in diethyl pyrocarbonate (DEPC)-treated water. For some experiments, poly($A^+$) RNA was subsequently isolated using the Poly(A) Tract System following manufacturer's instructions (Promega).

mRNA Differential display—Differential display was performed following the protocol of Liang and Pardee (Liang, P. et al. (1992) $Science$ 257, 967–971). Briefly, 50 $\mu$g of total RNA isolated from either of three populations of $C.$ $elegans$, controls or those grown in the presence of cadmium for 8 h or 24 h, was treated with 10 units of RNase-free DNase I (Boehringer Mannheim) in 10 mM Tris-Cl buffer, pH 8.3, containing 50 mM KCl and 1.5 mM $MgCl_2$. The DNA-free RNA was precipitated with ethanol and dissolved in DEPC-treated water. First-strand cDNAs were generated in reverse transcriptase reactions containing 0.2 $\mu$g DNA-free total RNA, reverse transcriptase buffer (25 mM Tris-Cl, pH 8.3, 38 mM KCl, 1.5 mM $MgCl_2$, 5 mM dithiothreitol), 5 $\mu$M of each dNTP and 1 $\mu$M of one of four 3'-degenerate anchored oligo (dT) primers. The 3'-degenerate anchored oligo (dT) primers have the sequence: $T_{12}MG$, $T_{12}MA$, $T_{12}MT$, or $T_{12}MC$, where M is 3-fold degenerate for G, A, and C. Primers were annealed to the RNA template by incubating the reaction mixture for 5 min at 65° C., then for 10 min at 37° C. First strand cDNA synthesis was achieved following the addition of 100 units of Moloney murine leukemia virus reverse transcriptase (GIBCO/BRL) and incubating at 37° C. for 50 min. The reaction was terminated by heating at 95° C. for 5 min, which inactivates the reverse transcriptase.

Amplification of cDNA fragments was performed in 20 $\mu$l reactions. Each PCR mixture contained 2 $\mu$l of the products from one of the four above reverse transcriptase reactions and 18 $\mu$l of a solution containing Taq-PCk buffer (10 mM Tris-Cl, pH 8.4, 50 mM KCl, 1.5 mM $MgCl_2$, 0.01% gelatin), 1 $\mu$M of the same 3'-degenerate anchored oligo(dT) primer used in the first-strand synthesis reaction, four dNTPs (2 $\mu$M each), 10 $\mu$Ci [$\alpha$-$^{35}$S]dATP (Amersham), 1 unit AmpliTaq DNA polymerase (Perkin-Elmer) and 0.2 $\mu$M of one of twenty 5'-arbitrary decamers. The sequences of the 5' arbitrary primer used in these reactions are presented in Table I. Reaction mixtures were subjected to 40 cycles of the PCR using the following parameters: denature at 94° C. for 30 seconds, anneal at 42° C. for 2 min, elongate at 72° C. for 30 seconds. All PCRs were performed in duplicate. The amplified cDNAs produced from duplicate reactions of RNA isolated from control, 8 h-treated and 24 h-treated $C.$ $elegans$ were size fractionated in parallel by polyacrylamide gel electrophoresis in 6% acrylamide/8M urea gels.

TABLE I

Sequences of the 5'-Arbitrary Decamer Primers used in Differential Display

| Primer Designation | Sequence |
| --- | --- |
| AP-3 | AGGTGACCGT (SEQ ID NO: 53) |
| AP-4 | GGTACTCCAC (SEQ ID NO: 54) |
| AP-6 | GCAATCGATC (SEQ ID NO: 55) |
| AP-7 | CCGAAGGAAT (SEQ ID NO: 56) |
| AP-8 | GGATTGTGCG (SEQ ID NO: 57) |
| AP-9 | CGTGGCAATA (SEQ ID NO: 58) |
| AP-10 | TAGCAAGTGC (SEQ ID NO: 59) |
| AP-13 | AGTTAGGCAC (SEQ ID NO: 60) |
| AP-15 | AGGGCCTGTT (SEQ ID NO: 61) |
| AP-18 | CTGAGCTAGG (SEQ ID NO: 62) |
| RT-1 | TACAACGAGG (SEQ ID NO: 63) |
| RT-2 | TGGATTGGTC (SEQ ID NO: 64) |
| RT-3 | CTTTCTACCC (SEQ ID NO: 65) |
| RT-4 | TTTTGGCTCC (SEQ ID NO: 66) |
| RT-5 | GGAACCAATC (SEQ ID NO: 67) |
| RT-6 | AAACTCCGTC (SEQ ID NO: 68) |
| RT-7 | TCGATACAGG (SEQ ID NO: 69) |
| RT-8 | TGGTAAAGGG (SEQ ID NO: 70) |
| RT-9 | TCGGTCATAG (SEQ ID NO: 71) |
| RT-10 | GGTACTAAGC (SEQ ID NO: 72) |

Following electrophoresis, gels were dried onto Whatman 3MM paper and exposed to Kodak X- AR film for 24 h. Differentially expresses cDNAs were visualized by autoradiography. To isolate differentially expressed cDNA fragments, regions of dried gels corresponding to the cDNAs were excised. Gel slices were rehydrated in 100 µl dH$_2$O following a 10-min incubation at room temperature. The cDNA was then extracted from the rehydrated gels by incubating at 100° C. for 15 min in tightly capped microcentrifuge tubes. cDNA was recovered by ethanol precipitation in the presence of 0.3M sodium acetate and 50 µg of glycogen (Boehringer Mannheim) . The eluted cDNA was reamplified in a 40 µl reaction with the identical pair of primers used in the mRNA differential display reaction. PCR reaction conditions were similar to those above except, the concentration of the dNTPs was increased to 20 µM and the [α-$^{35}$S] dATP was omitted. Amplified cDNA fragments were resolved by gel electrophoresis using a 1.5% agarose gel and then purified using QIAEXII kits (QIAGEN)

Subcloning and DNA sequence analysis—Gel-purified cDNAs were directly inserted into the T-A cloning vector pGEM-T (Promega). DNA inserts were subsequently sequenced using T7 and SP6 primers by the dideoxynucleotide chain termination procedures of Sanger et. al (Sanger, F. et al. (1977) Proc. Natl. Acad. Sci. U.S.A. 74, 5463–5467) (United States Biochemicals Sequenase Kit, Version 2.0).

Computer analysis—Analysis of cDNA sequence data including sequence comparisons, alignments and generation of contigs were performed using PC/GENE-Intelli-Genetics software. BLAST analysis (Altschul, S. F. et al. (1990) J. Mol. Biol. 215, 403–410) was carried out through the National Center for Biotechnology Information and the C. elegans Genome Project Internet servers using the nonredundant, C. elegans genome and C. elegans EST databases. For some sequence analysis the "A C. elegans database" (ACeDB) software was used (Eeckman, F. H. et al. (1995) Methods Cell. Biol. 48, 583–605). Predicted C. elegans genes were identified by the C. elegans Genome Project using the GENEFINDER program (Favello, A. et al. (1995) Methods Cell. Biol. 48, 551–569).

Northern Blot Analysis-Samples of total RNA (20 µg) or poly(A$^+$) RNA (2 µg) were denatured in a 2.2M formaldehyde/50% (v/v) formamide buffer and then subjected to denaturing gel electrophoresis on a 1.5% agarose/2.2M formaldehyde gel. Size-fractionated RNAs were then transferred to Nytran membrane (Schleicher and Schuell). Membranes were probed with $^{32}$P-labeled cDNA fragments of the differentially expressed mRNAs. cDNAs to be used as probes were generated by the PCR from the cloned DNA fragments recovered from differential display gels. cDNAs were labeled with [α-$^{32}$]dCTP (Amersham) by random-primed labeling. Membranes were hybridized in 6 ×SSC (1×SSC=0.15M sodium chloride, 15 mM sodium citrate, pH 7.0), 1.25× Denhardt's solution, 0.5% sodium dodecyl sulfate (SDS), 300 ng denatured sonicated salmon sperm DNA and heat-denatured probe at 42° C. for 16 h. Following hybridization, membranes were washed at a high stringency of 50° C. for 30 min in 0.1×SSC/0.1% SDS. The amount of probe hybridizing to the RNA was determined by Phospho-rImager analysis (Molecular Dynamic System) . After images were obtained, membranes were incubated at 95° C. for 1 h in 0.1% SDS to remove the bound probe. They were then hybridized with a $^{32}$P-labeled C. elegans myosin light-chain probe, which served as a loading control (Freedman, J. H. et al. (1993) J. Biol. Chem. 268, 2554–2564). As a positive control, membranes were also hybridized to a $^{32}$P-labeled C. elegans metallothonein-2 (mtl-2) cDNA probe (Freedman, J. H. et al. (1993) J. Biol. Chem. 268, 2554–2564). Quantification of radioactivity was performed using the ImageQuant program (Molecular Dynamic System). Steady-state levels of mRNA expression were all normalized to that of the constitutively expressed myosin light-chain mRNAs (Freedman, J. H. et al. (1993) J. Biol. Chem. 268, 2554–2564; Cummins, C. et al. (198B) Mol. Cell. Biol 8, 5334–5349).

Reverse-Northern dot-blot analysis—Changes in the steady-state levels of differentially expressed mRNAs in C. elegans following cadmium-exposure were also determined by reverse-Northern dot-blot analysis by the modified procedure of Zhang et al. (Cummins, C. et al. (1988) Mol. Cell. Biol 8, 5334–5349). Briefly, differentially expressed cDNAs that were previously cloned into pGEM-T were amplified using primers that anneal to the T7 and SP6 RNA polymerase binding sites, which flank the cDNA insert. cDNAs were amplified and subsequently purified using a PCR-spin column (QIAGEN). Approximately 100 ng of each amplified cDNA were denatured by mixing with 0.1N NaOH (final concentration) and incubating at 100° C. for 5 min. The solution was neutralized following the addition of 3×SSC (final concentration) and then the volume adjusted to 700 µl with dH$_2$O. 200-µl of each sample was applied to one of three Nytran membranes in a Bio-Dot microfiltration apparatus (BioRad). Membranes were then baked for 30 min at 80° C. under vacuum. As positive and loading controls 100 ng of mtl-1 cDNA and myosin light chain DNA were also applied to each membrane, respectively.

Three pools of single-stranded $^{32}$P-labeled cDNA probes were prepared from poly(A$^+$) RNA isolated from control, 8 h and 24 h cadmium-treated nematodes. cDNAs were generated from a mixture of mRNAs in a 25 µl reverse transcriptase reactions which contained 2 µg poly(A$^+$) RNA, 1 µg oligo (dT)$_{18}$ primer, reverse transcriptase buffer, 800 µM DATP, dGTP and dTTP, 4.5 µM dCTP, 100 µCi [α-$^{32}$P]dCTP (3000 Ci/mmol), 20 units RNase inhibitor and 200 units Moloney murine leukemia virus reverse transcriptase. The reaction mixture was incubated at 37° C. for 1 h, then at 95° C. for 5 min to terminate the reaction. Unincorporated nucleotides were separated from the labeled cDNAs by using a G-25 spin column (Boehringer Mannheim). Equal amounts (5×10⁶ cpm/ml) of each radioactive cDNA mixture were heat-denatured and then hybridized separately to one of the three membranes at 42° C. for 16 h in hybridization buffer. Membranes were washed at a high stringency of 0.1×SSC, 0.1% SDS at 55° C. for 30 min. The amount of $^{32}$P-labeled probe bound to each differentially expressed cDNA was quantified by PhosphorImager analysis and levels of expression of the cognate mRNAs normalized to that of the myosin light-chain mRNA.

EXAMPLE 1

Effect of Cadmium on Gene Expression

Figure 1:
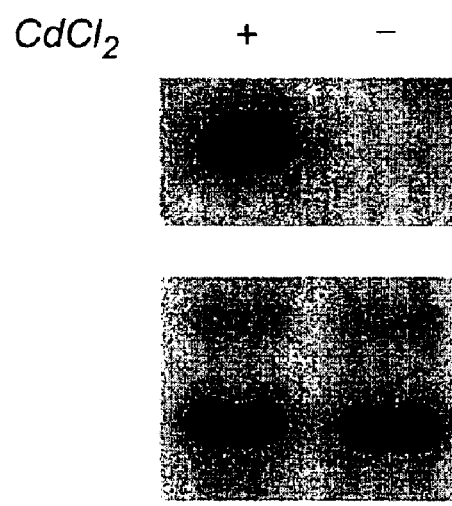
FIG. 1. Confirmation of cadmium-responsive gene expression. Total RNA was extracted from control C.

The level of the *C. elegans* mtl-2 mRNA was measured by Northern blot analysis to confirm that the cadmium-exposure protocol outlined above affects gene expression (Freedman, J. H. et al. (1993) *J. Biot. Chem.* 268, 2554–2564). A $^{32}$P-labeled oligonucleotide probe that is specific for the 3'-end of the mtl-2 mRNA was hybridized to a membrane that contained RNA prepared from control *C. elegans* or nematodes exposed to 100 μM CdCl$_2$ for 24 h (FIG. 1). The steady-state level of mtl-2 mRNA increased in response to cadmium exposure to that previously reported (Freedman, J. H. et al. (1993) *J. Biol. Chem.* 268, 2554–2564). This verified that the cadmium-treatment protocol alters gene expression in *C. elegans* and can be used for the differential display analysis.

EXAMPLE 2

Identification of Cadmium-responsive Genes by Differential Display mRNA expression patterns of non-treated *C. elegans* and those exposed to cadmium for 8 h and 24 h were compared by mRNA differential display in order to identify new genes whose transcription is regulated by cadmium. A total of twenty 5'-arbitrary decamers, including five that have sequences that are homologous to the mtl-1 cDNA, were used. Each of the twenty decamers was paired with one of four 3'-degenerate anchored oligo(dT) primers and used to amplify cDNAs prepared from control and cadmium-treated *C. elegans*. All amplification experiments were performed in duplicate using RNA prepared from independently treated populations of *C. elegans*. This generated a total of 480 separate reactions: three populations of cDNA amplified using eighty combinations of primers, in duplicate.

To bias against isolating differentially displayed cDNAs that are "false positive" (Liang, P. (1993) *Nucleic Acids Res.* 21, 3269–3275), only cDNAs whose level of expression were affected by cadmium in duplicate experiments were selected for further analysis. In addition, cDNA fragments that have altered levels of expression in both the 8 h and 24 h cadmium-treated samples were selected. Representative data is presented in FIG. 2. A total of seventy-five differentially expressed cDNA fragments were identified and excised from the gels. Of the cDNAs that were selected for further evaluation, the majority showed an increase in band intensity as a result of cadmium treatment, compared to identical sized DNA fragments from the control sample. A single product, VL9, was identified that showed decreased band intensity in the cadmium-treated *C. elegans* cDNA compared to the control.

Fifty-three cDNAs were successfully extracted from the acrylamide gels, reamplified and cloned. Because of the large number of cDNAs successfully isolated, no further attempt was made to clone the remaining fragments. The cloned cDNA fragments ranged in size 141 bp to 326 bp (Table II). These cDNAs were subsequently sequenced, and changes in the in vivo steady-state level of expression of the cognate mRNAs following cadmium treatment evaluated.

TABLE II

Changes in the steady-state level of differentially expressed mRNAs

| Clone name | Primers used in PCR | Size of PCR product (bp) | Fold-change in mRNA levels following cadmium exposure[a] | |
|---|---|---|---|---|
| | | | 8 hours | 24 hours |
| DDRT1 | T$_{12}$MG/RT-4 | 255 | 2.2 | 3.2 |
| DDRT2●[b] | T$_{12}$MG/RT-4 | 214 | 3.1 | 3.9 |
| DDRT3▲ | T$_{12}$MC/RT-5 | 162 | 2.0 | 2.4 |
| DDRT4▲ | T$_{12}$MC/RT-5 | 187 | 2.5 | 2.8 |
| DDRT5 | T$_{12}$MA/RT-5 | 254 | 3.2 | 3.9 |
| DDRT6 | T$_{12}$MC/RT-5 | 219 | 4.7 | 5.0 |
| DDRT7● | T$_{12}$MG/RT-6 | 217 | 3.6 | 4.0 |
| DDRT9 | T$_{12}$MA/RT-6 | 240 | 3.5 | 2.8 |
| DDRT10 | T$_{12}$MC/RT-7 | 212 | 2.7 | 2.5 |
| DDRT12 | T$_{12}$MA/RT-7 | 226 | 3.0 | 3.2 |
| DDRT15 | T$_{12}$MG/RT-10 | 248 | 2.8 | 3.1 |
| DDRT16● | T$_{12}$MG/RT-10 | 240 | 4.3 | 4.9 (3.5)[c] |
| DDRT17 | T$_{12}$MA/RT-10 | 200 | 3.7 | 5.7 |
| DDRT18 | T$_{12}$MC/RT-10 | 228 | 2.2 | 2.9 |
| DDRT19■ | T$_{12}$MT/AP-3 | 322 | 2.7 | 3.9 |
| DDRT20■ | T$_{12}$MT/AP-3 | 213 | 2.6 | 2.8 |
| DDRT21U | T$_{12}$MC/AP-4 | 284 | 2.2 | 2.6 |
| DDRT21D | T$_{12}$MC/AP-4 | 188 | 2.2 | 4.2 |
| DDRT22 | T$_{12}$MC/AP-4 | 292 | 2.5 | 3.3 |
| DDRT23▼ | T$_{12}$MG/AP-4 | 277 | 3.3 | 3.0 |
| DDRT24 | T$_{12}$MG/AP-4 | 272 | 1.3 | 1.5 |
| DDRT25♦ | T$_{12}$MA/AP-13 | 228 | 3.9 | 4.4 |
| DDRT26● | T$_{12}$MG/AP-13 | 238 | 4.4 | 4.7 |
| DDRT28♦ | T$_{12}$MA/AP-13 | 308 | 1.7 | 1.8 |
| DDRT29 | T$_{12}$MG/AP-15 | 141 | 3.9 | 4.4 |
| DDRT30 | T$_{12}$MA/AP-15 | 289 | 2.7 | 3.1 |
| DDRT32▼ | T$_{12}$MT/AP-15 | 252 | 2.6 | 2.4 |
| DDRT33U | T$_{12}$MG/AP-18 | 208 | 3.0 | 3.5 |
| DDRT33D | T$_{12}$MG/AP-18 | 171 | 3.1 | 3.5 |
| DDRT34 | T$_{12}$MA/AP-18 | 189 | 2.4 | 3.0 |
| DDRT35 | T$_{12}$MT/AP-18 | 314 | 1.6 | 1.9 |
| DDRT36+ | T$_{12}$MC/AP-18 | 292 | 1.1 | 1.1 |
| DDRT37 | T$_{12}$MC/AP-4 | 267 | 1.0 | 1.2 |
| DDRT38▼ | T$_{12}$MC/AP-4 | 238 | 1.1 | 1.8 |
| DDRT40 | T$_{12}$MA/AP-8 | 264 | 1.9 | 2.3 |
| DDRT41 | T$_{12}$MA/AP-8 | 154 | 2.2 | 2.1 |
| DDRT47+ | T$_{12}$MC/AP-13 | 165 | 1.5 | 1.4 |
| DDRT48▼ | T$_{12}$MG/AP-13 | 232 | 2.1 | 2.6 |
| DDRT50 | T$_{12}$MT/AP-15 | 254 | 2.2 | 2.2 |
| VL1★ | T$_{12}$MT/AP-6 | 217 | (4.7) | (5.2) |
| VL3 | T$_{12}$MT/AP-6 | 199 | 1.4 | 2.4 |
| VL5★ | T$_{12}$MT/AP-7 | 216 | ND[c] | ND |
| VL7★ | T$_{12}$MT/AP-7 | 217 | ND | ND |
| VL8★ | T$_{12}$MC/AP-6 | 214 | ND | ND |
| VL9 | T$_{12}$MT/AP-6 | 356 | -1.7 | -2.3 |
| VL10★ | T$_{12}$MT/AP-7 | 196 | ND | ND |
| VL11 | T$_{12}$MT/AP-7 | 142 | 3.2 | 6.1 |
| VL12★ | T$_{12}$MG/AP-10 | 216 | ND | 5.2 |
| VL13★ | T$_{12}$MG/AP-9 | 216 | ND | ND |
| VL15★ | T$_{12}$MT/AP-10 | 217 | ND | ND |
| VL19 | T$_{12}$MG/AP-9 | 285 | 3.6 | 5.0 (2.3) |
| VL20 | T$_{12}$MT/AP-9 | 148 | 2.8 | 5.0 |
| VL21 | T$_{12}$MC/AP-10 | 326 | 2.2 | 2.5 (2.0) |

[a]Steady-state levels of differential expressed RNAs were determined by reverse-Northern blot analysis. Fold-change in expression is relative to non-exposed *C. elegans*. All values have been normalized to the level of myosin light chain mRNA and are the average of three independent experiments.
[b]Clones labeled with identical symbols (●■▼♦▲★+) indicate that the differentially expressed cDNAs are derived from the same gene (see Table III).
[c]Values in parenthesis were determined by Northern blot analysis.
[d]ND; Not determined.

EXAMPLE 3

Northern and Reverse-Northern Blot Analyses with Differentially Displayed cDNA Fragments Northern blot analysis was initially used to confirm that the differentially expressed cDNA fragments, VL3, VL9, VL11, VL19, VL20, VL21 and DDRT16, represent mRNAs whose steady-state levels change following cadmium exposure in vivo. RNA blots were prepared with either size fractionated total RNA or poly(A+) mRNA, which were isolated from control and cadmium exposed C. elegans, and probed with $^{32}$P-labeled cDNA fragments. Northern blot analysis confirmed that as a result of cadmium treatment, the levels of expression of VL19 and DDRT16 increase 2.3-fold and 3.5-fold, respectively (FIG. 3). There is also a 2-fold increase in the level of VL21 mRNA. The mRNAs for VL3, VL9, VL11 and VL20 were not detected by Northern blots containing poly(A+) mRNA isolated from either control or cadmium-treated C. elegans.

Reverse-Northern dot-blot analysis (Zheng, H. et al. (1996) Nucleic Acids Res. 24, 2454–2455) was performed as an alternative to traditional Northern blots. In this analysis, all of the differentially expressed clones as well as positive and loading controls were simultaneously examined. Representative results are shown in FIG. 4, and Table II summarizes the quantitative analysis from three separate experiments.

C. elegans mtl-1 and myosin light chain DNAs were used as controls in the reverse-Northern dot-blot analysis. The mtl-1 mRNA is induced ~5-fold after cadmium treatment (FIG. 4), while the level of expression of myosin light-chain mRNA remained constant. These results are consistent with those previously reported (Freedman, J. H. et al. (1993) J. Biol. Chem. 268, 2554–2564).

Of the fifty-three cDNA fragment isolated, forty-six of the clones corresponded to C. elegans RNAs whose level of expression increased ~2- to 5-fold following an 8-h cadmium-treatment, and up to 6-fold after a 24-h exposure (Table II). Two differentially expressed mRNAs, VL3 and DDRT38, do not show any significant change in expression following an 8 h cadmium exposure, compared to control nematodes. After a 24 h exposure, however, there is an ~2-fold increase in their levels of expression. The level of expression for VL9 decreased ~2-fold in response to cadmium. These results confirm that the changes in the levels RNA observed by differential display analysis reflect the in vivo molecular response of C. elegans to cadmium. Four of the clones, DDRT24, DDRT36, DDRT37 and DDRT47, did not significantly change their level of expression after either 8 h or 24 h cadmium exposure (Table II). These clones are defined as false positives.

EXAMPLE 4

Nucleotide Sequencing and Homology Searching

The nucleotide sequences of the differentially expressed DNA fragments were compared against the C. elegans genomic and EST databases. Only seven of the cDNA fragments, DDRT12, DDRT15, DDRT21D, DDRT29, DDRT41, VL3 and VL21 did not show a >95% sequence identity to regions of the C. elegans genome (Table III). Forty-four clones were identical to C. elegans cosmid and/or yeast artificial chromosome (YAC) sequences. In addition, thirty-nine clones were identical to C. elegans ESTs (26 of 39) or predicted genes (32 of 39).

TABLE III

Sequence analysis of cadmium-regulated, differentially expressed cDNAs

| Clone name | Cosmid[b] | Sequence Identity/Homology[a] Gene product[c] | GenBank accession no.[h] |
|---|---|---|---|
| DDRT1 | T09B4 | T09B4.1, CELK00886 | AF071359 |
| DDRT2●[d] | F35E8 | F35E8.11 | AF071362 |
| DDRT3▲ | F35E12 | F35E12.7 | AF071382 |
| DDRT4▲ | F35E12 | F35E12.7 | AF071391 |
| DDRT5 | C56C10 | C56C10.12, CELK05910 | AF071396 |
| DDRT6 | W03C9 | W03C9.5, CELK06396 | AF071397 |
| DDRT7● | F35E8 | F35E8.11 | AF071398 |
| DDRT9 | C35D10 | ND[e] | AF071399 |
| DDRT10 | C49C3 | ND | AF071353 |
| DDRT12 | ND | ND | AF071354 |
| DDRT15 | ND | ND | AF071355 |
| DDRT16● | F35E8 | F35E8.11 | AF071356 |
| DDRT17 | C49A9 | C49A9.4, CELK02276 | AF071358 |
| DDRT18 | F13G4 | F13G3.4, CELK06645 | AF071360 |
| DDRT19■ | ZK849 | ND | AF071361 |
| DDRT20■ | ZK849 | ND | AF071363 |
| DDRT21U | Y111B2[f] | ND | AF072438 |
| DDRT21D | ND | CELK05123 | AF071364 |
| DDRT22 | F57G9 | ND | AF071365 |
| DDRT23▼ | F31C3 | C. elegans rDNA tandem repeats | AF071376 |
| DDRT24 | C56C10 | C56C10.8; CELK02788; Human transcription factor BTF3g | AF071377 |
| DDRT25♦ | R119 | R119.5; CELK00686 | AF071378 |
| DDRT26● | F35E8 | F35E8.11 | AF071379 |
| DDRT28♦ | R119 | R119.5; CELK00686 | AF071380 |
| DDRT29 | ND | ND | AF071138 |
| DDRT30 | C27H5 | C27H5.5; CELK02088, C. elegans collagen (col-36) | AF071383 |
| DDRT32▼ | F31C3 | C. elegans rDNA tandem repeats | AF071384 |
| DDRT33D | C34F6 | CELK01885; C. elegans cuticle collagen | AF071385 |
| DDRT34 | F20C5 | F20C5.1; CELK01295 | AF071386 |
| DDRT35 | R11D1 | R11D1.1; CELK02809; Human hypothetical protein KIAA0174 | AF071387 |

TABLE III-continued

Sequence analysis of cadmium-regulated, differentially expressed cDNAs

| Clone name | Cosmid[b] | Gene product[c] Sequence Identity/Homology[a] | GenBank accession no.[h] |
|---|---|---|---|
| DDRT36+ | D2096 | D2096.8; CELK01725; Human nucleosome assembly protein 1 LIKE-1 | AF071388 |
| DDRT37 | K11H12 | K11H12.2; CELK02043; Rat 60S ribosomal protein | AF071389 |
| DDRT38▼ | F31C3 | *C. elegans* rDNA tandem repeats | AF071390 |
| DDRT40 | W02B3 | W02B3.2; Bovine β-adrenergic receptor kinase | AF071392 |
| DDRT41 | ND | *Spiroplasma citr* DNA gyrase subunit B | AF071393 |
| DDRT47+ | D2096 | D2096.8; CELK01725; Human nucleosome assembly protein 1 LIKE-1 | AF071394 |
| DDRT48▼ | F31C3 | *C. elegans* rDNA tandem repeats | AF071395 |
| VL1★ | K11G9 | K11G9.5; CELK3309; *C. elegans* metallothionein-1(mtl-1) | AF073166 |
| VL3 | ND | ND | AF071374 |
| VL5★ | K11G9 | K11G9.5; CELK3309; *C. elegans* metallothionein-1(mtl-1) | AF071375 |
| VL7★ | K11G9 | K11G9.5; CELK3309; *C. elegans* metallothionein-1(mtl-1) | AF072436 |
| VL8★ | K11G9 | K11G9.5; CELK3309; *C. elegans* metallothionein-1(mtl-1) | AF072437 |
| VL9 | C50B6 | ND | AF071375 |
| VL10 | K11G9 | K11G9.5; CELK3309; *C. elegans* metallothionein-1(mtl-1) | AF073167 |
| VL11 | C06G3 | C60G3.8 | AF073168 |
| VL12★ | K11G9 | K11G9.5; CELK3309; *C. elegans* metallothionein-1(mtl-1) | AF072434 |
| VL13★ | K11G9 | K11G9.5; CELK3309; *C. elegans* metallothionein-1(mtl-1) | AF073169 |
| VL15★ | K11G9 | K11G9.5; CELK3309; *C. elegans* metallothionein-1(mtl-1) | AF072435 |
| VL19 | D2023 | D2023.2; CELK00011; Human pyruvate carboxylase | AF073170 |
| VL20 | B0228 | B0228.1 | AF071371 |
| VL21 | — | CELK00200; *C. elegans* mitochondrial hsp70 protein F precursor | AF071372 |

[a]Analyzed with BLASTN using GenBank and *C. elegans*-specific databases. The sequences have >80% nucleotide sequence identity.
[b]*C. elegans* genomic cosmids that have >90% nucleotide sequence identity.
[c]Predicted genes are designated by the cosmid name followed by the structural gene number (e.g., F35E8.11). *C. elegans* ESTs are denoted with the "CELK" designation.
[d]Clones labeled with identical symbols (●■▼♦▲★+) indicate that the differentially expressed cDNAs are derived from the same gene.
[e]ND, Not detected.
[f]Yeast Artificial Chromosome
[g]Homologous proteins are presented that have a >60% amino acid sequence identity, based on BLASTX analysis.
[h]See FIG. 5

The results of the BLASTN analysis showed that the differentially expressed cDNA fragments were derived from thirty-two independent genes (Table III). Eight cDNA clones, VL1, VL5, VL7, VL8, VL10, VL12, VL13 and VL15, are identical to the mtl-1 cDNA sequence. This result is not unexpected because five of the 5'-random decamer primers used in the amplification reactions are identical, or have a one-nt mismatch, to regions in the mtl-1 cDNA. These primers were specifically selected to function as internal controls which amplified the mtl-1 cDNA, in order to confirm the efficacy of differential display analysis in identifying cadmium-responsive *C. elegans* genes.

Four clones, DDRT2, DDRT7, DDRT16 and DDRT26, are derived from the predicted gene F35E8.11. They were amplified using the same 3'-degenerate oligo(dT) primer, however, four different 5'-primers were used (Table II). In several cases, pairs of cDNA fragments were isolated that are products of the same gene, DDRT3 and DDRT4; DDRT19 and DDRT20; and DDRT25 and DDRT28. The lengths of the cDNA fragments in each pair are different. Each pair of cDNA products was, however, amplified using identical pair of primers (Table II). Four cDNA fragments were isolated that have sequences that are homologous to the *C. elegans* rDNA tandem repeats in cosmid F31C3. The sequences of two of the clones, DDRT23 and DDRT38, are identical. The sequences of these rDNAs are homologous to a region in the cosmid between nt 25265 and 25433. The sequences of clones DDRT48 and DDRT32 are not homologous to the other rDNA clones. They are identical to regions of the cosmid approximately 3 kb from the region homologous to DDRT23 and DDRT38, nt 28041–28245 and nt 28634–28887, respectively.

cDNA fragments isolated using the differential display technique typically contain 3'-untranslated regions of the mRNAs. In order to identify proteins that are encoded by these mRNAs, we took advantage of *C. elegans* cDNA Project data. The nucleotide sequences of many of the cadmium-responsive mRNAs are identical to cDNA clones isolated and sequenced by the Project. By assembling contigs consisting of the differentially expressed cDNA sequence and the related *C. elegans* EST sequences, longer open-reading frames were generated. For example, the differentially expressed clone DDRT33D is 171 bp and its sequence is 100% identical to the 3'-end of the *C. elegans* clone yk58b1. This clone is a member of a group of six related cDNA clones (cDNA group: CELK01885) for which 3' and 5' sequence data is available. This EST data was collected and assembled into a single 880 bp contig that was analyzed by BLASTX (the clones within the CELK01885 cDNA group are yk364f10 (GenBank Accession Number C69593 and GenBank Accession Number C58303), yk279e3 (GenBank Accession Number C68110 and GenBank Accession Number C57084), yk363b2 (GenBank Accession Number C69396 and GenBank Accession Number C58214), yk146f5 (GenBank Accession Number C10425), yk92a12 (GenBank Accession Number D66109 and GenBank Accession Number D69777) and yk58b1 (GenBank Accession Number D65495 and GenBank Accession Number D68941)). This protocol was used for the analysis of clones DDRT1, DDRT21D, DDRT24, DDRT25, DDRT35, DDRT36, VL19 and VL21

The results of the BLASTX analysis are presented in Table III. Cadmium exposure causes an increase in the steady-state levels of a several *C. elegans* proteins that are homologous to proteins in the protein databases: Clone VL21 corresponds to a mRNA that encodes the *C. elegans* HSP70F protein precursor. The expression of HSP70 has been shown to increase following cadmium exposure in mammalian cells (Wiegant. F. A. et al. (1994) *Toxicology* 94, 143–159; Hiranuma, K. et al. (1 993) *Biochem. Biophys. Res. Commun.* 194, 531–536). This response, however, has not been reported in *C. elegans*. Cadmium exposure also induced the expression of a mRNA that encodes a DNA gyrase homologue, DDRT41. The metal caused a 3-fold increase in the levels of mRNAs DDRT30 and DDRT33D that encode two different *C. elegans* collagens (col-36 and a predicted cuticle collagen, respectively). It also affected mRNAs that encode proteins that are homologous to a β-adrenergic receptor kinase (DDRT40), pyruvate carboxylase (VL19) and the hypothetical human protein KIAA0174 (DDRT35). BLASTX analysis of the remaining differentially expressed cDNAs did not find significant homologies between the translated sequences and those in the non-redundant GenBank database Thus, the majority of the cadmium responsive, differentially expressed cDNAs encode novel proteins.

All documents cited above are hereby incorporated in their entirety by reference, as are all sequences referenced by accession number (e.g., GenBank Accession Number).

One skilled in the art will appreciate from a reading of this disclosure that various changes in form and detail can be made without departing from the true scope of the invention.

What is claimed is:

1. An isolated nucleic acid comprising the sequence of DDRT2 (SEQ ID NO:34).

2. An isolated nucleic acid comprising the sequence of DDRT7 (SEQ ID NO:50).

3. An isolated nucleic acid comprising the sequence of DDRT16 (SEQ ID NO:40).

4. An isolated nucleic acid comprising the sequence of DDRT26 (SEQ ID NO:14).

5. An isolated mRNA encoded by the nucleic acid of claim 1.

6. An isolated mRNA encoded by the nucleic acid of claim 2.

7. An isolated mRNA encoded by the nucleic acid of claim 3.

8. An isolated mRNA encoded by the nucleic acid of claim 4.

* * * * *

SEQUENCE LISTING

<160> NUMBER OF SEQ ID NOS: 72

<210> SEQ ID NO 1
<211> LENGTH: 165
<212> TYPE: DNA
<213> ORGANISM: Artificial Sequence
<220> FEATURE:
<223> OTHER INFORMATION: Description of Artificial Sequence: Probe

<400> SEQUENCE: 1

```
tttttttttt ttttccaacc ccttcacata ataggcggaa aaccgattgt tgctgttact      60
tgttgttgtg tttattccct gacctatcca tattcccttc ttcccaatct ctaaagatat     120
acctgaaaac gagtttttg aatacttgat acatttgtct tcatc                     165
```

<210> SEQ ID NO 2
<211> LENGTH: 154
<212> TYPE: DNA
<213> ORGANISM: Artificial Sequence
<220> FEATURE:
<223> OTHER INFORMATION: Description of Artificial Sequence: Probe

<400> SEQUENCE: 2

```
tggattgtgc gggtggtact gccaagtctg gtcgtgatag aaaacatcag gcgatcatgc      60
ctttacgtgg taagatcctg aacgtcgaaa agcaatggaa cataagatct acgaaaatga     120
ggagatcaaa aacatgttta cagctttggt ccta                                 154
```

<210> SEQ ID NO 3
<211> LENGTH: 264
<212> TYPE: DNA
<213> ORGANISM: Artificial Sequence
<220> FEATURE:
<223> OTHER INFORMATION: Description of Artificial Sequence: Probe

<400> SEQUENCE: 3

```
tggattgtgc ggagtataag caaaaatttc tggaaaagtc gggtgatatg aagtttgata      60
agatcttcaa tcaaaagctc ggtttcttgt tgttaaaaga ttccgcagga aaatgtctcc     120
gagagtccgt gtcctcaaat taaattctac gaggcgatca aagaatacga gaaatggag     180 acaccagatg agcgattaac aaaagcacga gaaatttatc gatcatcata tacggttgaa     240
ttccgtcgcg caatcgtcac actc                                            264
```

<210> SEQ ID NO 4

```
<211> LENGTH: 187
<212> TYPE: DNA
<213> ORGANISM: Artificial Sequence
<220> FEATURE:
<223> OTHER INFORMATION: Description of Artificial Sequence: Probe

<400> SEQUENCE: 4
aaatttttat taaaataaaa taaacatgtt tttgttgata ttatagcgtt aaagctgaaa      60
tgacaatgat tagaaaacca gcagagaata gagatgatgt tcctttcgtt gttgtttcca    120
gtgaacactt gttgcggtgg agcccgtatt tagcgagtgg tagttttttga tgtgattggt   180
tccaatc                                                              187

<210> SEQ ID NO 5
<211> LENGTH: 267
<212> TYPE: DNA
<213> ORGANISM: Artificial Sequence
<220> FEATURE:
<223> OTHER INFORMATION: Description of Artificial Sequence: Probe

<400> SEQUENCE: 5
tggtactcca cctacaagtt ctacaagttc tacgaggttg tcctgatcga tccattccac     60
aaggctatcc gtcgtaaccc agacacccaa tggatcacca gcctagttc acaagcaccg    120
tgagcaaaga ggactcacct ctgctggacg caagttcgtg gactcggaaa gggattgctt   180
ttctctgcta cccgcggagg atcccaacac caaagttttt ccacccgcca accgataaat   240
cttgttattt tattttgttt tgggttt                                        267

<210> SEQ ID NO 6
<211> LENGTH: 292
<212> TYPE: DNA
<213> ORGANISM: Artificial Sequence
<220> FEATURE:
<223> OTHER INFORMATION: Description of Artificial Sequence: Probe

<400> SEQUENCE: 6 ttttttttt ttttcccaac cccttcacat aaaggcggaa aaccgattgt tgctgttact      60
tgttgttgtc gtttattccc tgaggtatcc atattccgct tctcccaatc tctaaagata   120
tacctgaaaa cgagttgtcg tcgaaatact tgatacatgt tgtcttcatc ctggtgtatg   180
ttgtttcgca aattcttcat actagttatg ataggatttg aatgagctgg cacgagtcaa   240
ctttgaactc gaatttcaat attttcgtga tcctgcatta agtgatgaat aa            292

<210> SEQ ID NO 7
<211> LENGTH: 314
<212> TYPE: DNA
<213> ORGANISM: Artificial Sequence
<220> FEATURE:
<223> OTHER INFORMATION: Description of Artificial Sequence: Probe

<400> SEQUENCE: 7
tctgagctag gaggtccagg aggaaacaac ggaggaggtg ctggaaatgg tggattcgac     60
gattttgatg atttggctcg ccgtttcgaa gaactgaaaa agattaagta atcatcaccc   120
gacgttccat tccttattaa ctatttgttt ctcttccacc caattttttt ttcacgtgtc   180
ttttttttgta tcataaatga accccccaaa aactagctgt ttcttagtgc atacgttaaa   240
acccctttag tcattgatta tcattgtata cctcattatc cgaaaaacct tcgacattc    300
atcaactagg tttt                                                      314
```

```
<210> SEQ ID NO 8
<211> LENGTH: 189
<212> TYPE: DNA
<213> ORGANISM: Artificial Sequence
<220> FEATURE:
<223> OTHER INFORMATION: Description of Artificial Sequence:  Probe

<400> SEQUENCE: 8
tctgagctag ggaccgaaat tcacaaatat ccaattgtta ctggatggtg gggatgtgga      60
cgatttaatg gggacaagcc actgaagtgt atgttatttc attcgttaaa tatgaagatg     120
gaggagagtg aatggggatt ttgcttcttt tgcaaaatgg cctccctatg tacctgaaaa     180
aaaaaaaaa                                                             189

<210> SEQ ID NO 9
<211> LENGTH: 171
<212> TYPE: DNA
<213> ORGANISM: Artificial Sequence
<220> FEATURE:
<223> OTHER INFORMATION: Description of Artificial Sequence:  Probe

<400> SEQUENCE: 9
tctgagctag gaaaggacgg agaagatgga gagaacggag ctgctggagc cgctggacca      60
aagggatctt gcgaccactg cccaccacca cgcactcccc aggatattaa ttcacttctc     120
tctaatttta gtgaatctca ttctaataaa agccgcccc aaaaaaaaaa a               171

<210> SEQ ID NO 10
<211> LENGTH: 289
<212> TYPE: DNA
<213> ORGANISM: Artificial Sequence
<220> FEATURE:
<223> OTHER INFORMATION: Description of Artificial Sequence:  Probe

<400> SEQUENCE: 10
tttttttttt tttgagcgag cgtttattat ttgagtcgag cttgggttga gtcgtcagct      60
gaacatgaag attgacaaag aagacgatca gcagcaacag atgcgcagag tcgcattctt     120
tgcggttgct gtctcaactg cagccgtcat ttcaagcatc gtgactctcc caatgatcta     180
ctcttactct tcaatctttc caatcccatt tgatcattgg aaaccgagtt ctgtaaaact     240
gtgctcgtga tatgtggtgt cgaagttctc cacaagtcag gtgtaccct               289

<210> SEQ ID NO 11
<211> LENGTH: 162
<212> TYPE: DNA
<213> ORGANISM: Artificial Sequence
<220> FEATURE:
<223> OTHER INFORMATION: Description of Artificial Sequence:  Probe

<400> SEQUENCE: 11
ctccaccgca acaagtgttc acgtggaaac aacaacgaaa ggaacatcat ctctatctct      60
gctggttttc taatcattgt catttcagct ttaacgctat aatcaacaaa aacagtttat     120
tttattttaa taaaaattta ttcgtgcaaa aaaaaaaaaa aa                        162

<210> SEQ ID NO 12
<211> LENGTH: 140
<212> TYPE: DNA
<213> ORGANISM: Artificial Sequence
<220> FEATURE:
<223> OTHER INFORMATION: Description of Artificial Sequence:  Probe

<400> SEQUENCE: 12
```

```
tagggcctgg ttgtgacaat gtgcactaaa atggggcatg aatatcacca gcagagttca      60
cttacccaaa gtgtacttat taagagtcaa ctgtgaagta tatgagacat ttcagttgcc     120
tgcccaaaaa aaaaaaaaaa                                                 140

<210> SEQ ID NO 13
<211> LENGTH: 308
<212> TYPE: DNA
<213> ORGANISM: Artificial Sequence
<220> FEATURE:
<223> OTHER INFORMATION: Description of Artificial Sequence: Probe

<400> SEQUENCE: 13
tagttaggca caggatgtac gaggaaattc tactattttc gggtctcacc acgaaatcac      60
aataacccgg attttttagt ggtccccgca cgttgaccta ctggcgcgtc aggcactccg     120
ccgcgacatt cgccgacacg cctacaatcc acgtgtcaat cgtcagattt gcggatcaat     180
aatggtgatg aaaggtggaa atacgtatat ggatcatgtt caaaggcatc aagctgaaca     240
attcgaagag ttgaatcggc gtcgacactt ttgatccaag accgtaagaa atttgaaagc     300
tattggtg                                                             308

<210> SEQ ID NO 14
<211> LENGTH: 238
<212> TYPE: DNA
<213> ORGANISM: Artificial Sequence
<220> FEATURE:
<223> OTHER INFORMATION: Description of Artificial Sequence: Probe

<400> SEQUENCE: 14
tttttttttt ttttggggag gaaatcacgg cttcggatgc aacagtcttc tctcaattgg      60
caactgtcta ttatccattc cgcaatcaca tttcggatgt tctcgaaaag gacttcccaa     120
agttattgga gtactgtgaa agagttcgtc atgaagttta cccaaaggac tttactatgt     180
gaattaaatt gtcaaactag tagtcagatc aataaaattt tccgcgcgaa aaaaaaaa      238

<210> SEQ ID NO 15
<211> LENGTH: 324
<212> TYPE: DNA
<213> ORGANISM: Artificial Sequence
<220> FEATURE:
<223> OTHER INFORMATION: Description of Artificial Sequence: Probe

<400> SEQUENCE: 15
tagttaggca caggatgtac gaggaaattc tactattttc gggtctcacc acgaaatcac      60
aataacccgg attttttagt ggtccccgca cgttgaccta cttggcgcgt caggcactcc     120
gccgcgacat tcgccgacac gcctacaatc cacgtgtcaa tcgtcagatt tgcggatcaa     180
taatggtgat gaaaggtgga atacgtata tggatcatgt tcaaaggcat caagctgaac      240
aattcgaaga gttgaatcgg cgtcgacaac ttttgatcc aagaccgtaa gaatttgaa      300 agctattggt gaaaaaaaaa aaaa                                            324

<210> SEQ ID NO 16
<211> LENGTH: 272
<212> TYPE: DNA
<213> ORGANISM: Artificial Sequence
<220> FEATURE:
<223> OTHER INFORMATION: Description of Artificial Sequence: Probe

<400> SEQUENCE: 16
tggtactcca cgcagaaaga agaaggtcat ccacaacacc gctactaccg atgacaagaa      60
```

```
gcttcaaagc aatttgaaga aactctctgt caccaacatt ccaggaatcg aggaggtcaa      120
catgattaag acgatggaac cgttatccac ttcaacaacc caaaagtcta aacctctgtt      180
cccagccaat accttctctg tcacaggatc agccgataac aagtcagatc actgaaatgt      240
ctcccaggga atgctgaact ggtcagagtc ct                                    272

<210> SEQ ID NO 17
<211> LENGTH: 218
<212> TYPE: DNA
<213> ORGANISM: Artificial Sequence
<220> FEATURE:
<223> OTHER INFORMATION: Description of Artificial Sequence: Probe

<400> SEQUENCE: 17
tttttttttt tttcgacaag cggggactaa aagcaagctt ttcatccacc gatgatacaa       60
ggcgttttta gtaccttagg atcgactgac ccacatccaa ctactgttcc acgtggaacc      120
cttctccact tcagtcttca aggatcgaac ttgaatattt gctactacca tacgatctgc      180
actgacggaa agtccagccg agcctacctc atagttaa                              218

<210> SEQ ID NO 18
<211> LENGTH: 238
<212> TYPE: DNA
<213> ORGANISM: Artificial Sequence
<220> FEATURE:
<223> OTHER INFORMATION: Description of Artificial Sequence: Probe

<400> SEQUENCE: 18
tttttttttt ttttgccggg cggtgtgtac aaccggcagg gacgtaatca acgtgagctg       60
atgactcgcg cttactaggc attcctcgtt taagggcaat aattacaata ccctatcccg      120
gacatggaag aatttcaacg gtttaccgat acctttcaac acgggaaaac tacccggttg      180
gacaccatta ggactgacag attgaaagtc tttgtcgatt tggtggttgg ttgtgcat       238

<210> SEQ ID NO 19
<211> LENGTH: 253
<212> TYPE: DNA
<213> ORGANISM: Artificial Sequence
<220> FEATURE:
<223> OTHER INFORMATION: Description of Artificial Sequence: Probe

<400> SEQUENCE: 19
tagggcctgt tggttgatgc ttgtccggcg cagttctgtc tgcttgatac ttcgggttga       60
tggcggacta gtgattgtgc ttcttgcgga ccgtttctgg tgtgtgcttg gacctcggtt      120
ctagtatcct gatcgctcat ctatcaaccg tactgtaacc ggtacgactc agggaatccg      180
actgtctaat taaacagag gtgacagatg gtccttgcgg acgttaactg tcactgattt      240
ctccccagtg cac                                                         253

<210> SEQ ID NO 20
<211> LENGTH: 277
<212> TYPE: DNA
<213> ORGANISM: Artificial Sequence
<220> FEATURE:
<223> OTHER INFORMATION: Description of Artificial Sequence: Probe

<400> SEQUENCE: 20
tttttttttt tttgggggggg gcggtgtgta caaagggcag ggacgtaatc aacgtgagct       60
gatgactcac acttctaggc attcctcgtt taagggaata attacaatac ccatcccgga      120
```

| | |
|---|---|
| catggaagaa tttcaacggt ttaccgatac cctttcggca acacgggaaa actcacccgg | 180 |
| tccggacacc attaggactg acagattgaa agctctttct cgatttggtg gttggtggtg | 240 |
| catggccgtt cttagttggt ggagtaccaa tcactag | 277 |

<210> SEQ ID NO 21
<211> LENGTH: 216
<212> TYPE: DNA
<213> ORGANISM: Artificial Sequence
<220> FEATURE:
<223> OTHER INFORMATION: Description of Artificial Sequence: Probe

<400> SEQUENCE: 21

| | |
|---|---|
| tagcaagtgc ggagacaaat gtgaatgcag tggagacaag tgttgtgaga agtactgctg | 60 |
| tgaggaggcc agtgagaaaa aatgctgtcc agctggatgt aagggagact gcaagtgtgc | 120 |
| aaactgtcat tgtgcagagc agaagcagtg cgagacaaga cccatcaaca ccagggaact | 180 |
| gctgcggctc attaaaatgt ttcagagttg aatcta | 216 |

<210> SEQ ID NO 22
<211> LENGTH: 356
<212> TYPE: DNA
<213> ORGANISM: Artificial Sequence
<220> FEATURE:
<223> OTHER INFORMATION: Description of Artificial Sequence: Probe

<400> SEQUENCE: 22

| | |
|---|---|
| caatcgatga gtatcctcgt acaattaatg catgatgcaa ttggaaatat tccgaggtag | 60 |
| gtaaaacggg gaacatcacg agatagatga atacagcgga tatcatatag gcacgcagaa | 120 |
| tatcaataaa attttcaaat tttcaaaata tcataacgat tataacacgt agcagggaat | 180 |
| tttaaagcca ctgaaataaa tatagaataa tatatacaga cacacacaat ctagatttca | 240 |
| gaacattttc agtaacgacg tttgaacttt tttgaagatt tcgccgagcc tttgatcact | 300 |
| tttgcagtca caacttccac aactttcttt tcctcctctt cctctacatc gattgc | 356 |

<210> SEQ ID NO 23
<211> LENGTH: 199
<212> TYPE: DNA
<213> ORGANISM: Artificial Sequence
<220> FEATURE:
<223> OTHER INFORMATION: Description of Artificial Sequence: Probe

<400> SEQUENCE: 23

| | |
|---|---|
| taaactctat gtttatttgt tttttcaaat ttcaaattga aaattgaaac tttcaatttg | 60 |
| attagagtct ttgtggtttg actcctttt ttcattgaac atcttttacg tacgtcatac | 120 |
| ttttgtatac acatttacaa atgttgtttt gtaattatat gtaacaaatt tctatgtaca | 180 |
| cctcatctca tctctctat | 199 |

<210> SEQ ID NO 24
<211> LENGTH: 326
<212> TYPE: DNA
<213> ORGANISM: Artificial Sequence
<220> FEATURE:
<223> OTHER INFORMATION: Description of Artificial Sequence: Probe

<400> SEQUENCE: 24

| | |
|---|---|
| cgtctccctt ttttacttac ttgtaggtgc gtcttgtcaa ttgtacgtac ttatatttag | 60 |
| caaacctctg gtgttacctc tgctttttg taaaatttgt tacacacttt cttttggca | 120 |
| gtaaaagttg tttagcacac tttaacactc tgccactacc aagtaatag tgagcccatc | 180 |

-continued

```
gaggttttat aaatgtcctt gatagtttaa agtgttggag gatcgagcta ctttggtagt       240
ggaaagccgt gtttcttgtc ttgttttgtt cgatgattta cccaactatt tgatattttg       300
atttaccgga ttatataata caccccc                                           326
```

<210> SEQ ID NO 25
<211> LENGTH: 147
<212> TYPE: DNA
<213> ORGANISM: Artificial Sequence
<220> FEATURE:
<223> OTHER INFORMATION: Description of Artificial Sequence: Probe

<400> SEQUENCE: 25

```
tggcaatata cctagaaaga gtaaatatta tgacgtggca ataatacaga agcagtccga       60
actacaactc acgaaacatt tgaaagttt acctcttgat ttcttttgaa tgttttgtct        120
cacacaataa agaaaattct accgtac                                           147
```

<210> SEQ ID NO 26
<211> LENGTH: 285
<212> TYPE: DNA
<213> ORGANISM: Artificial Sequence
<220> FEATURE:
<223> OTHER INFORMATION: Description of Artificial Sequence: Probe

<400> SEQUENCE: 26

```
cgtggcaata cacagaatat acacattgag atggttcgaa tggcaaagag aaggtggtgg      60
ctaatcattc tatatagcac aacgccaaat ataatttcga tgtggcggaa tttgtgatgg      120
tgaatggaat taacaaaatt ttctaaacgt cttcattccg agtaattttt cgttttccct      180
ccacttttcg atttatattg ttttcttaga aaaagtattt attgcatcgg gtgctcattg      240
tctttgtgta gaatataaac tcgttcactt cccaaaaaaa aaaaa                      285
```

<210> SEQ ID NO 27
<211> LENGTH: 216
<212> TYPE: DNA
<213> ORGANISM: Artificial Sequence
<220> FEATURE:
<223> OTHER INFORMATION: Description of Artificial Sequence: Probe

<400> SEQUENCE: 27

```
tagcaagtcg gagacaaatg tgaatgcagt ggagacaagt gttgtgagaa gtactgctgt      60
gaggaggcca gtgagaaaaa atgctgtcca gctggatgta agggagactg caagtgtgca     120
aactgtcatt gtgcagagca gaagcagtgc ggagacaaga cccatcaaca ccagggaact     180
gctgcggctc attaaaatgt ttcagagttg aatcta                                216
```

<210> SEQ ID NO 28
<211> LENGTH: 142
<212> TYPE: DNA
<213> ORGANISM: Artificial Sequence
<220> FEATURE:
<223> OTHER INFORMATION: Description of Artificial Sequence: Probe

<400> SEQUENCE: 28

```
gtgctggagt tgtttgtatt tcagaataaa taaaataaaa tatgatttga gtagaatatt      60
aaaataaagt ccttcacatt aaattatcaa ttgcttggcc tcgaatatct tccagctggt     120
gattgcattc gttcattcct tc                                               142
```

<210> SEQ ID NO 29

<211> LENGTH: 84
<212> TYPE: DNA
<213> ORGANISM: Artificial Sequence
<220> FEATURE:
<223> OTHER INFORMATION: Description of Artificial Sequence: Probe

<400> SEQUENCE: 29
tagcaagtgc ggagacaaat gtgaatgcag tggagacaag tgttgtgaga agtactgctg    60
tgaggattcc agtgagaaaa aatc    84

<210> SEQ ID NO 30
<211> LENGTH: 217
<212> TYPE: DNA
<213> ORGANISM: Artificial Sequence
<220> FEATURE:
<223> OTHER INFORMATION: Description of Artificial Sequence: Probe

<400> SEQUENCE: 30
tagcaagtgc ggagacaaat gtgaatgcag tggagacaag tgttgtgaga agtactgctg    60
tgaggaggcc agtgagaaaa aatgctgtcc agctggatgt aagggagact gcaagtgtgc   120
aaactgtcat tgtgcagagc agaagcagtg cggagacaag acccatcaac accagggaac   180
tgctgcggct cattaaaatg tttcagagtt gaatcta                            217

<210> SEQ ID NO 31
<211> LENGTH: 292
<212> TYPE: DNA
<213> ORGANISM: Artificial Sequence
<220> FEATURE:
<223> OTHER INFORMATION: Description of Artificial Sequence: Probe

<400> SEQUENCE: 31
tggtactcca cacggacaaa tacatttagt tttacaagcc gccacgcgac acgcaacgcc    60
gtaaatctac caaggtacaa caacaacatg tcaagcacag acccatatct tatttgtgcg   120
gaacgagatg gcctctactg tagtaatcga caattggact cttatccacc ggatcactta   180
acctattttg atattaatat tcctattggg atcacagggt ttgcccgaaa atgtaattat   240
gaactgaatt gaaatgtatt ataaattagt ttttattggg aaaaaaaaa aa            292

<210> SEQ ID NO 32
<211> LENGTH: 188
<212> TYPE: DNA
<213> ORGANISM: Artificial Sequence
<220> FEATURE:
<223> OTHER INFORMATION: Description of Artificial Sequence: Probe

<400> SEQUENCE: 32
tataggttaa gtgatccggt ggataagagt ccaattgtcg attactacag tagaggccat    60
ctgcttccgc acaaataaga tatgggtctg tgcttgacat gttgttgttg taccttgggt   120
agatttacgg cagttgcgtg tcgttggcgg cttgtaaaac taaatgtatt tttccgtgtg   180
gagtacca                                                            188

<210> SEQ ID NO 33
<211> LENGTH: 289
<212> TYPE: DNA
<213> ORGANISM: Artificial Sequence
<220> FEATURE:
<223> OTHER INFORMATION: Description of Artificial Sequence: Probe

<400> SEQUENCE: 33
tttttttttt ttttgtacat tatggcaaat ggaggcactg tctggttccg tggggtcatg    60

```
gtgcattgga tcatggtata tcctatcctg gcttctaatc ccaatgcgtt tacagtcatg   120
tgggcttgaa cgggcctagc tgagcttgga caaagttcct tgacagtacg ggtcgacaag   180
cttgacagtc agaaattagg cacttgtggg ctacaggtgc tcgtaattat tttgagagtt   240
ctgggcttcc ggacttttac taggctaatc taagacaact gggctctaa               289
```

<210> SEQ ID NO 34
<211> LENGTH: 214
<212> TYPE: DNA
<213> ORGANISM: Artificial Sequence
<220> FEATURE:
<223> OTHER INFORMATION: Description of Artificial Sequence: Probe

<400> SEQUENCE: 34

```
aaatcatggc ggcggatgca acagtcttct caattggcaa ctgtctatat cattccgcaa   60
cacatttcgg atgttctcga aaggacttc ccaaagttat tggagtactg tgaaagagtt   120
cgtcatgaag tttcccaaag gactttacta tgtgaattaa attgtcaaac tagtagtcag   180
atcaataaaa ttttacgtgg aaaaaaaaaa aaaa                               214
```

<210> SEQ ID NO 35
<211> LENGTH: 322
<212> TYPE: DNA
<213> ORGANISM: Artificial Sequence
<220> FEATURE:
<223> OTHER INFORMATION: Description of Artificial Sequence: Probe

<400> SEQUENCE: 35

```
taggtgaccg tagagaagcc cagatattta aaatctaaag ggaaactgtt tgaccagaag   60
attagagccc agttgtctta gatagcctag taaaagtccg gaagcccaga actctcaaaa   120
taattacgag cacctgtagc ccacaagtgc ctaatttctg actgtcaagc ttgtcgaccc   180
gtactgtcaa ggaactttgt caagctcagc taggcccgtt caagcccaca tgactgtaaa   240
cgattcggga ttagaagcca ggataggata tccatgatcc aatgcaccat gacccacgga   300
accagatgtg ctcattacat ag                                            322
```

<210> SEQ ID NO 36
<211> LENGTH: 228
<212> TYPE: DNA
<213> ORGANISM: Artificial Sequence
<220> FEATURE:
<223> OTHER INFORMATION: Description of Artificial Sequence: Probe

<400> SEQUENCE: 36

```
tttttttttt tttccccatt catcacacac tatcatgttt tatattcaga cctattacct   60
gtccagaaaa actgagctga aaaaatcccg gacgagcagc tccttcacat tcaaaatctt   120
ccatcatttc cccactcaat tcatttgttt tgtctttgat tttcaaattt tttgccttat   180
tattttattg ctaaattaag aaaactgtta ctttgcaaaa aaaaaaa                 228
```

<210> SEQ ID NO 37
<211> LENGTH: 255
<212> TYPE: DNA
<213> ORGANISM: Artificial Sequence
<220> FEATURE:
<223> OTHER INFORMATION: Description of Artificial Sequence: Probe

<400> SEQUENCE: 37

```
atcattcaag aaagctatta tcagaaaaca taaatgacat agatcaagtg taaatcacat   60
```

-continued

```
atatataaag tggataaata tatatagtta aacggataag gaaattaatt aatgaatttt      120
gaaactggca gcgaaggatg aacagggaaa ggcacatgtt aaaataaatg aatgtgtata      180
atttcgtgaa gagttagtta tgttaggtga tggcagccat gcagaatgag ccattgttcc      240
gaaaaaaaaa aaaaa                                                       255

<210> SEQ ID NO 38
<211> LENGTH: 433
<212> TYPE: DNA
<213> ORGANISM: Artificial Sequence
<220> FEATURE:
<223> OTHER INFORMATION: Description of Artificial Sequence: Probe

<400> SEQUENCE: 38
tggtactaag ggccaataac tgagcttttg cacggcggca tcaatgataa agagaaacta       60
tttttgacgg ttaaaataac caaatttaca ccggcgagtc aatcaaaaat tctcatctgg      120
aacagcaaag tacatcggag aattgctgga aggaagcact gatgaaacta aattaactgc      180
tggatgcata ggaaaaacgt caagattgac gtggagttgg agagaaggac tatgtttgga      240
tggttactaa gattttgtaa ctggtgacaa taaggacatc actttctaa ctaacttaaa       300 ttcttttttta cttcttttct tctgaattaa ttgtgtttta aggcgaattc tatgtttcag      360
aatttattta cgtttgcttt tcatgttta attgtaaaag taagcaattt ttccaccgta       420
aaaaaaaaaa aaa                                                        433

<210> SEQ ID NO 39
<211> LENGTH: 933
<212> TYPE: DNA
<213> ORGANISM: Artificial Sequence
<220> FEATURE:
<223> OTHER INFORMATION: Description of Artificial Sequence: Probe

<400> SEQUENCE: 39
catgcatctt ttttttttt ttttttttta ctgtctcaag tatgttggat tcatgtttga       60
ttattactgc tgcgctgttt ggagccgctg tcatttactt gaaaaatttc ttcactgttc      120
ctagcattaa accaaaacct gatattcaca aaaaagacta caaaaaggat gtagtctatc      180
tgtatcagat gaagagactc aagaactgtc cgaacttgtc cccttttctgc atgaaaatcg     240 agattctttg tagaatcttc aagattcctt acgagattat cacatgcacc tctgaacgct     300
ctcggaatgg attggtccct ttcgttgaac tcaatggaga gcacattgct gattctgatc     360
ttatcgaaat gcgcttgaga tcacatttta aaattccgtc gcttccaact gagctggaaa     420
ctcaatctgt tgctctaagc aagtttgcag atcaccattt gttcttcgta cttatacgat     480
ttaaaattgc tgtcgacgaa ttctacaaaa ccattatcga ataatcggt ctcccaacct      540 tcctgaattt ccttctcatg ccccttttga aggctataat cgggaaaaat gtctacaaca     600
aatgtcaggg agccattgga gattttgaat tgagtgagct cgacgagatt cttcacagag     660
atttgcgaat cgtagagaac accttggcca agaaaaagtt tcttttcggg gaggaaatca     720
cggcggcgga tgcaacagtc ttctctcaat tggcaactgt ctattatcca ttccgcaatc     780
acatttcgga tgttctcgaa aaggacttcc caaagttatt ggagtactgt gaaagagttc     840
gtcatgaagt ttacccaaag gactttacta tgtgaattaa attgtcaaac tagtagtcag     900
atcaataaaa ttctacgtgg caaaaaaaaa aaa                                 933

<210> SEQ ID NO 40
<211> LENGTH: 238
```

```
<212> TYPE: DNA
<213> ORGANISM: Artificial Sequence
<220> FEATURE:
<223> OTHER INFORMATION: Description of Artificial Sequence: Probe

<400> SEQUENCE: 40
tttttttttt tttgggagga aatcacggcg gcggatgcaa cagtcttctc tcaattggca      60
actgtctatt atccattccg caatcacatt tcggatgttc tcgaaaagga cttcccaaag    120
ttattggagt actgtgaaag agttcgtcat gaagtttacc caaaggactt tactatgtga    180
attaaattgt caaactagta gtcagatcaa taaaattcta cgtggcaaaa aaaaaaaa     238

<210> SEQ ID NO 41
<211> LENGTH: 248
<212> TYPE: DNA
<213> ORGANISM: Artificial Sequence
<220> FEATURE:
<223> OTHER INFORMATION: Description of Artificial Sequence: Probe

<400> SEQUENCE: 41
tttttttttt tttcgcatgt tgtaatacta atatttatta attttcttta attttctttg      60
ttaagtttgt atttataggt tgttgagatt tttttgcctg taattttgca actgtgattc    120
atgtatgtac tatatgaacc gaaaccccct cccgtcatac acaacagtta gtaaaacatt    180
ttaatcccat atttctcatt cccaacactc ttacaggttt tgcatcagca gcagcagtgc    240
aaacacaa                                                             248

<210> SEQ ID NO 42
<211> LENGTH: 226
<212> TYPE: DNA
<213> ORGANISM: Artificial Sequence
<220> FEATURE:
<223> OTHER INFORMATION: Description of Artificial Sequence: Probe

<400> SEQUENCE: 42
tttttttttt ttttgtaaca aagaactgag cactctatgg tttatcaagt ctatatgtat      60
ccgtgatgcc tactgtatcg tacatccatc tcgatcgtaa tgcattattg atcatgagtt    120
cccaaaggtc ttaatcttga caaggtgca atagatatat atccttattt ggcactatat    180
atatgttcag aattatgact gatcgataca tatgatcaaa gttaca                  226

<210> SEQ ID NO 43
<211> LENGTH: 212
<212> TYPE: DNA
<213> ORGANISM: Artificial Sequence
<220> FEATURE:
<223> OTHER INFORMATION: Description of Artificial Sequence: Probe

<400> SEQUENCE: 43
ttcgatacag gaactacatt tacatctgtt tcaacatatc aacaatacat aacatactca      60
atccttcagg ctctgaagga ttttgagtgc gatatactgt aacaagctcg ggaaacataa    120
gtacattttt tggagctatc ttttatgtt gcgcttttct tttgtctctt tgaatgagtt    180
ttgaaatgaa ttgtctgtgc aaaaaaaaaa aa                                  212

<210> SEQ ID NO 44
<211> LENGTH: 284
<212> TYPE: DNA
<213> ORGANISM: Artificial Sequence
<220> FEATURE:
<223> OTHER INFORMATION: Description of Artificial Sequence: Probe
```

```
<400> SEQUENCE: 44
tggtactcca cacggacaaa tacatttagt tttacaagcc gccacgcgac acgcaacggc      60
cgtaaatcta cccaaggtac aacaacaaca tgtcaagcac agacccatat cttatttgtg     120
cggaaggatg gcctctactg tagtaatcga caattggact cttatccacc ggatcactta     180
acctattttg atattaatat gcctgattgg ggatcacagg gtttgcccga aaatgtaatt     240
atgaactgaa ttcgaaatgt atttataaat tagttttttat tggg                     284

<210> SEQ ID NO 45
<211> LENGTH: 214
<212> TYPE: DNA
<213> ORGANISM: Artificial Sequence
<220> FEATURE:
<223> OTHER INFORMATION: Description of Artificial Sequence:  Probe

<400> SEQUENCE: 45
gcaagtgcgg agacaaatgt gaatgcagtg gagacaagtg ttgtgagaag tactgctgtg      60
aggaggccag tgagaaaaaa tgctgtccag ctggatgtaa gggagactgc aagtgtgcaa     120
actgtcattg tgcagagcag aagcagtgcg agacaagacc catcaacacc agggaactgc     180
tgcggctcat taaaatgttt cagagttgaa tcta                                 214

<210> SEQ ID NO 46
<211> LENGTH: 217
<212> TYPE: DNA
<213> ORGANISM: Artificial Sequence
<220> FEATURE:
<223> OTHER INFORMATION: Description of Artificial Sequence: Probe

<400> SEQUENCE: 46
ttagcaagtg cggagacaaa tgtgaatgca gtggagacaa gtgttgtgag aagtactgct      60
gtgaggaggc cagtgagaaa aaatgctgtc cagctggatg taagggagac tgcaagtgtg     120
caaactgtca ttgtgcagag cagaagcagt gcgagacaag acccatcaac accagggaac     180
tgctgcggct cattaaaatg tttcagagtt gaatcta                              217

<210> SEQ ID NO 47
<211> LENGTH: 217
<212> TYPE: DNA
<213> ORGANISM: Artificial Sequence
<220> FEATURE:
<223> OTHER INFORMATION: Description of Artificial Sequence:  Probe

<400> SEQUENCE: 47
ttagcaagtg cggagacaaa tgtgaatgca gtggagacaa gtgttgtgag aagtactgct      60
gtgaggaggc cagtgagaaa aaatgctgtc cagctggatg taagggagac tgcaagtgtg     120
caaactgtca ttgtgcagag cagaagcagt gcgagacaag acccatcaac accagggaac     180
tgctgcggct cattaaaatg tttcagagtt gaatcta                              217

<210> SEQ ID NO 48
<211> LENGTH: 216
<212> TYPE: DNA
<213> ORGANISM: Artificial Sequence
<220> FEATURE:
<223> OTHER INFORMATION: Description of Artificial Sequence:  Probe

<400> SEQUENCE: 48
tagcaagtgc ggagacaaat gtgaatgcag tggagacaag tgttgtgaga agtactgctg      60
tgaggaggcc agtgagaaaa aatgctgtcc agctggatgt aagggagact gcaagtgtgc     120
```

```
aaactgtcat tgtgcagagc agaagcagtg cgagacaaga cccatcaaca ccagggaact    180
gctgcggctc attaaaatgt ttcagagttg aatcta                              216

<210> SEQ ID NO 49
<211> LENGTH: 240
<212> TYPE: DNA
<213> ORGANISM: Artificial Sequence
<220> FEATURE:
<223> OTHER INFORMATION: Description of Artificial Sequence: Probe

<400> SEQUENCE: 49
tttttttttt ttgagactat gaatatttaa tttagcaagc gaatttgttg ttattagata    60
ggaagcctag aagagtgaaa attttaaaaa atgtgaggaa ctggttttgt attcagaagc    120
atataaacgt tgtcttaatt tatatatgac gttctctatg aatatagcca aaatgatcga    180 tattttaat ccaaaaatca aacattttg gtatacgaac ctcgccttca cggaggttta     240

<210> SEQ ID NO 50
<211> LENGTH: 217
<212> TYPE: DNA
<213> ORGANISM: Artificial Sequence
<220> FEATURE:
<223> OTHER INFORMATION: Description of Artificial Sequence: Probe

<400> SEQUENCE: 50
tttttttttt ttttgggagg aaatcacggc ggcggatcga acagtcttct ctcaattggc    60
aactgtctat atcattccgc aatcacattt cggatgttct cgaaaaggca ttccaaagtt    120
attggagtca tgtgaaagag ttcgtcatga agtttaccca aaggcatttc atagtgaatt    180
aaattgtcaa actagtagtc agatcaataa aattttc                             217

<210> SEQ ID NO 51
<211> LENGTH: 219
<212> TYPE: DNA
<213> ORGANISM: Artificial Sequence
<220> FEATURE:
<223> OTHER INFORMATION: Description of Artificial Sequence: Probe

<400> SEQUENCE: 51
tttttttttt tttgacgaca aattatttag aaatattgca taagcgaaaa tacaatttga    60
cccgtagcaa aaaatacat gtcgggaaaa tgagaaaaat ggttaataaa tttttaaaaa    120
aagtatataa ttcctccaac aagctactgc atgtccttgt actacaatct tctccgacgg    180
attccactct cgatcgcgga ttcggattct tcatgttgg                           219

<210> SEQ ID NO 52
<211> LENGTH: 254
<212> TYPE: DNA
<213> ORGANISM: Artificial Sequence
<220> FEATURE:
<223> OTHER INFORMATION: Description of Artificial Sequence: Probe

<400> SEQUENCE: 52
tttttttttt tttttgccca tcggaaaata gcaagcctct ccacaggtac agtaattgag    60
catttggatg atgcttcttc acagcattat ccagtgtata cttatccttt ttcgtaagag    120
tttcgaaaaa atgtccataa aaagtgttga atgacttttg ttcatctcga agcatacata    180
cgatcgaaac ggagaaatcg atagatcgaa tcaggataag tggggatact gtattgtcgg    240
atgaaaacat agac                                                      254
```

<210> SEQ ID NO 53
<211> LENGTH: 10
<212> TYPE: DNA
<213> ORGANISM: Artificial Sequence
<220> FEATURE:
<223> OTHER INFORMATION: Description of Artificial Sequence: Probe

<400> SEQUENCE: 53
aggtgaccgt                                                          10

<210> SEQ ID NO 54
<211> LENGTH: 10
<212> TYPE: DNA
<213> ORGANISM: Artificial Sequence
<220> FEATURE:
<223> OTHER INFORMATION: Description of Artificial Sequence: Probe

<400> SEQUENCE: 54
ggtactccac                                                          10

<210> SEQ ID NO 55
<211> LENGTH: 10
<212> TYPE: DNA
<213> ORGANISM: Artificial Sequence
<220> FEATURE:
<223> OTHER INFORMATION: Description of Artificial Sequence: Probe

<400> SEQUENCE: 55
gcaatcgatc                                                          10

<210> SEQ ID NO 56
<211> LENGTH: 10
<212> TYPE: DNA
<213> ORGANISM: Artificial Sequence
<220> FEATURE:
<223> OTHER INFORMATION: Description of Artificial Sequence: Probe

<400> SEQUENCE: 56
ccgaaggaat                                                          10

<210> SEQ ID NO 57
<211> LENGTH: 10
<212> TYPE: DNA
<213> ORGANISM: Artificial Sequence
<220> FEATURE:
<223> OTHER INFORMATION: Description of Artificial Sequence: Probe

<400> SEQUENCE: 57
ggattgtgcg                                                          10

<210> SEQ ID NO 58
<211> LENGTH: 10
<212> TYPE: DNA
<213> ORGANISM: Artificial Sequence
<220> FEATURE:
<223> OTHER INFORMATION: Description of Artificial Sequence: Probe

<400> SEQUENCE: 58
cgtggcaata                                                          10

<210> SEQ ID NO 59
<211> LENGTH: 10
<212> TYPE: DNA
<213> ORGANISM: Artificial Sequence
<220> FEATURE:
<223> OTHER INFORMATION: Description of Artificial Sequence: Probe

```
<400> SEQUENCE: 59
tagcaagtgc                                                                  10

<210> SEQ ID NO 60
<211> LENGTH: 10
<212> TYPE: DNA
<213> ORGANISM: Artificial Sequence
<220> FEATURE:
<223> OTHER INFORMATION: Description of Artificial Sequence: Probe

<400> SEQUENCE: 60
agttaggcac                                                                  10

<210> SEQ ID NO 61
<211> LENGTH: 10
<212> TYPE: DNA
<213> ORGANISM: Artificial Sequence
<220> FEATURE:
<223> OTHER INFORMATION: Description of Artificial Sequence: Probe

<400> SEQUENCE: 61
agggcctgtt                                                                  10

<210> SEQ ID NO 62
<211> LENGTH: 10
<212> TYPE: DNA
<213> ORGANISM: Artificial Sequence
<220> FEATURE:
<223> OTHER INFORMATION: Description of Artificial Sequence: Probe

<400> SEQUENCE: 62
ctgagctagg                                                                  10

<210> SEQ ID NO 63
<211> LENGTH: 10
<212> TYPE: DNA
<213> ORGANISM: Artificial Sequence
<220> FEATURE:
<223> OTHER INFORMATION: Description of Artificial Sequence: Probe

<400> SEQUENCE: 63
tacaacgagg                                                                  10

<210> SEQ ID NO 64
<211> LENGTH: 10
<212> TYPE: DNA
<213> ORGANISM: Artificial Sequence
<220> FEATURE:
<223> OTHER INFORMATION: Description of Artificial Sequence: Probe

<400> SEQUENCE: 64
tggattggtc                                                                  10

<210> SEQ ID NO 65
<211> LENGTH: 10
<212> TYPE: DNA
<213> ORGANISM: Artificial Sequence
<220> FEATURE:
<223> OTHER INFORMATION: Description of Artificial Sequence: Probe

<400> SEQUENCE: 65
ctttctaccc                                                                  10

<210> SEQ ID NO 66
```

```
<211> LENGTH: 10
<212> TYPE: DNA
<213> ORGANISM: Artificial Sequence
<220> FEATURE:
<223> OTHER INFORMATION: Description of Artificial Sequence: Probe

<400> SEQUENCE: 66
ttttggctcc                                                              10

<210> SEQ ID NO 67
<211> LENGTH: 10
<212> TYPE: DNA
<213> ORGANISM: Artificial Sequence
<220> FEATURE:
<223> OTHER INFORMATION: Description of Artificial Sequence: Probe

<400> SEQUENCE: 67
ggaaccaatc                                                              10

<210> SEQ ID NO 68
<211> LENGTH: 10
<212> TYPE: DNA
<213> ORGANISM: Artificial Sequence
<220> FEATURE:
<223> OTHER INFORMATION: Description of Artificial Sequence: Probe

<400> SEQUENCE: 68
aaactccgtc                                                              10

<210> SEQ ID NO 69
<211> LENGTH: 10
<212> TYPE: DNA
<213> ORGANISM: Artificial Sequence
<220> FEATURE:
<223> OTHER INFORMATION: Description of Artificial Sequence: Probe

<400> SEQUENCE: 69
tcgatacagg                                                              10

<210> SEQ ID NO 70
<211> LENGTH: 10
<212> TYPE: DNA
<213> ORGANISM: Artificial Sequence
<220> FEATURE:
<223> OTHER INFORMATION: Description of Artificial Sequence: Probe

<400> SEQUENCE: 70
tggtaaaggg                                                              10

<210> SEQ ID NO 71
<211> LENGTH: 10
<212> TYPE: DNA
<213> ORGANISM: Artificial Sequence
<220> FEATURE:
<223> OTHER INFORMATION: Description of Artificial Sequence: Probe

<400> SEQUENCE: 71
tcggtcatag                                                              10

<210> SEQ ID NO 72
<211> LENGTH: 10
<212> TYPE: DNA
```

-continued

```
<213> ORGANISM: Artificial Sequence
<220> FEATURE:
<223> OTHER INFORMATION: Description of Artificial Sequence: Probe

<400> SEQUENCE: 72
ggtactaagc                                                            10
```